United States Patent [19]
Hollenberg et al.

[11] Patent Number: 5,516,889
[45] Date of Patent: May 14, 1996

[54] SYNTHETIC THROMBIN RECEPTOR PEPTIDES

[75] Inventors: Morley D. Hollenberg, Calgary, Canada; John M. Matsoukas, Patras, Greece; Graham J. Moore, Calgary, Canada

[73] Assignee: University Technologies International, Inc., Calgary, Canada

[21] Appl. No.: 405,933

[22] Filed: Mar. 17, 1995

Related U.S. Application Data

[63] Continuation of Ser. No. 80,643, Jun. 21, 1993, abandoned.
[51] Int. Cl.$^6$ ..................................................... C07K 7/64
[52] U.S. Cl. ............................................................. 530/317
[58] Field of Search .............................. 530/317; 514/11, 514/9

[56] References Cited

U.S. PATENT DOCUMENTS

| | | | |
|---|---|---|---|
| 4,661,471 | 4/1987 | Hawiger et al. | 514/13 |
| 4,861,865 | 8/1989 | Hortin | 530/326 |
| 5,071,954 | 12/1991 | Pelzer et al. | 530/324 |
| 5,084,273 | 1/1992 | Hirahara | 424/94.6 |
| 5,093,237 | 3/1992 | Enomoto | 435/13 |
| 5,138,035 | 8/1992 | Wakselman et al. | 530/317 |
| 5,256,766 | 10/1993 | Coughlin | 530/330 |

FOREIGN PATENT DOCUMENTS

| | | |
|---|---|---|
| 0291981 | 11/1988 | European Pat. Off. . |
| 0410541 | 1/1991 | European Pat. Off. . |
| WO 88/03151 | 5/1988 | WIPO . |
| WO 91/101331 | 2/1991 | WIPO . |
| WO 91/15515 | 10/1991 | WIPO . |
| WO 92/14750 | 9/1992 | WIPO . |
| WO 92/17196 | 10/1992 | WIPO . |

OTHER PUBLICATIONS

Peptides, Ali et al, Proceedings of the 11th Am. Pept. Symp., (Jul. 1989), La Jolla, Ca. pp. 94–96.

Muramatsu et al, Canadian Journal of Physiology and Pharmacology, vol. 70(7), (Jul. 1992), pp. 996–1003.

Chao, Biochemistry, vol. 31(27), (Jul. 1992), pp. 6175–6178.

Vassallo et al, The Journal of Biol. Chem., vol. 267(a), (Mar. 1992), pp. 6081–6085.

Ahlquist, R. P. A study of the adrenotropic receptors. Amer. J. Physiol. 153: 586–600 (1948).

Barlos K., Gatos, D., Hondrelis, J., Matsoukas, J. M., Moore, G. J., Schafer, W. and Sotiriou, P. Preparation of new acid labile resins of the secondary alcohol type and their application in peptide synthesis. *Liebigs Ann. Chem.*: 951–955 (1989).

Brass, L. F., et al. Structure and Function of the Human Platelet Thrombin Receptor, *J. Biol. Chem.* 267: 13795–13798 (1992).

Chao, B. H., S. Kalkunte, J. M. Maraganore, and S. R. Stone. Essential groups in synthetic agonist peptides for activation of the platelet thrombin receptor. Biochemistry 31: 6175–6178 (1992).

Coller, B. S., et al. Thrombin Receptor Activating Peptides: Importance of the N–Terminal Serine and Its Ionization State As Judged by pH Dependence, Nuclear Magnetic Resonance Spectroscopy, and Cleavage by Aminopeptidase M. Biochemistry 31: 11713–11720 (1992).

Coughlin, S. R., T.–K. Vu, D. T. Hung, and V. I. Wheaton. Characterization of a functional thrombin receptor. J. Clin. Invest. 89: 351–355 (1992).

deblois, D., G. Drapeau, E. Petitclerc, and Marceau, Francois. Synergism between the contractile effect of epidermal growth factor and that of des–Arg$_9$–bradykinin or of a α–thrombin in rabbit aortic rings. Brit. J. Pharmacol. 105: 959–967 (1992).

DeMey, J. G., M. Claeys, and P. M. Vanhoutte. Endothelium–dependent inhibitory effects of acetylcholine, adenosine triphosphate, thrombin and arachidonic acid in the canine femoral artery. J. Pharmacol. Exp. Ther. 222: 166–173 (1982).

Dimaio, J., F. R. Ahmed, P. Schiller, and B. Belleau. Stereoelectronic control and de–control of the opiate receptor. Recent Advances in Receptor Chemistry; F. Gualtieri, M. Giannella and C. Melchiorre, eds. 1979 Elsevier/North–Holland Biomedical Press. pp. 221–234 (1979).

Drapeau G., et al. Activity of the Newly Discovered Thrombin Receptor Agonist on the Rabbit Aorta. *Vascular Smooth Muscle Pharmacology* 1: 393–398 (1992).

Hollenberg, M. D., S.–G. Yang, A. A. Laniyonu, G. J. Moore, and M. Saifeddine. Action of thrombin receptor polypeptide in gastric smooth muscle: Identification of a core pentapeptide retaining full thrombin–mimetic intrinsic activity. Mol. Pharmacol. 42: 186–191 (1992).

Hui, K. Y., et al. Minimal Sequence Requirement of Thrombin Receptor Agonist Peptide. *Biochemical and Biophysical Research Comm.* 184: 790–796 (1992).

Hung, D. T., et al. Thrombin–induced Events in Non–Platelet Cells Are Mediated by the Unique Proteolytic Mechanism Established for the Cloned Platelet Thrombin Receptor. *J. Cell Biology* 116: 827–832 (1992).

Huston, J. S. et al. Protein Engineering of Antibody Binding Sites: Recovery of Specific Activity in an Anti–Digoxin Single–Chain Fv analogue Produced in Escherichia coli. *Proc. Natl. Acad. Sci USA* 85: 5879–5883 (1988).

Maraganore, J. M., et al. Thrombin Receptor Antagonist Peptides ('TRAPs') Derived From the Anion–Binding Exosite Domain of Human Thrombin. *Circulation* 86: 86,4: 1–867 (1992).

(List continued on next page.)

Primary Examiner—Howard E. Schain
Attorney, Agent, or Firm—Burns, Doane, Swecker & Mathis

[57] ABSTRACT

This invention relates to novel peptides based on a thrombin receptor sequence and novel methods for synthesis of these novel peptides. These peptides, branched-chain compounds and/or derivatized solid supports containing TRPs may be used diagnostically or therapeutically.

6 Claims, 4 Drawing Sheets

OTHER PUBLICATIONS

Matsoukas, J. M., M. H. Goghari, M. N. Scanlon, K. J. Franklin, and G. J. Moore. Synthesis and biological activities of analogs of angiotensin II and III containing O-methyl-troysine and D-tryptophan. J. Med. Chem. 28: 780–783 (1985).

Matsoukas, J. M., Agelis, G., Hondrelis, J., Yamdagni, R., Wu, Q., Ganter, R., Smith, J., Moore, D. and Moore, G. J. Synthesis and biological activities of angiotensin II, sarilesin and sarmesin analogues containing Aze or Pip at position 7. J. Med. Chem. 36: 904–911 (1993).

Matsoukas, J. M., Cordopatis, P., Belte, U., Goghari, M. N., Franklin, K. J. and Moore, G. J. Importance of the N-terminal domain of the type II angiotensin antagonist Sarmesin for receptor blockade. J. Med. Chem. 31: 1418–1421 (1988).

Muramatsu, I., H. Itoh, K. Lederis, and M. D. Hollenberg. Distinctive actions of epidermal growth factor-urogastrone in isolated smooth muscle preparations from guinea pig stomach: differential inhibition by indomethacin. J. Pharmacol. Exp. Ther. 245: 625–631 (1988).

Muramatsu, I., A. Laniyonu, G. J. Moore, and M. D. Hollenberg. Vascular actions of thrombin receptor peptide. Can. J. Physiol. Pharmacol. 70: 996–1003 (1992).

Rapoport, R. M., M. B. Draznin, and F. Murad. Mechanisms of adenosine triphosphate-, thrombin-, and trypsin-induced relaxation of rat thoracic aorta. Cir. Res. 55: 468–479 (1984).

Sabo, T., et al. Structure-Activity Studies of the Thrombin Receptor Activating Peptide. Biochemical and Biophysical Research Comm. 188: 604–610 (1992).

Savarese, T. M., and C. M. Fraser. In vitro mutagenesis and the search for structure function relationships among G protein-coupled receptors. Biochem. J. 283: 1–19 (1992).

Scarborough, R. M., et al. A Thrombin Receptor Antagonist Designed From Tethered Ligand Agonist Peptides. Circulation, 86: 86,4: 1–151 (1992).

Simonet, S., et al. Venous and arterial endothelial cells respond differently to thrombin and its endogenous receptor agonist. Eur. J. of Pharmacology 216:135–137 (1992).

Sugama, Y., et al. Thrombin Receptor 14-Amino Acid Peptide Mediates Endothelial Hyperadhesivity and Neutrophil Adhesion by P-Selectin-Dependent Mechanism. Circulation Research 71: 1015–1019 (1992).

Vassalo, R. R., Jr., T. Kieber–Emmons, K. Cichowsku, and L. F. Brass. Structure-function relationships in the activation of platelet thrombin receptors by receptor derived peptides. J. Biol. Chem. 267: 6081–6085 (1992).

Vouret–Craviari, V., E. Van Obberghen–Schilling, U. B. Rasmussen, A. Pavirani, J.-P. Lecocq, and J. Pouyssegur. Synthetic α–thrombin receptor peptides activate G-protein-–coupled signaling pathways but are unable to induce mitogenesis. Mol. Biol. Cell. 3: 95–102 (1992).

Vu, T.-K. H., D. T. Hung, V. I. Wheaton, and S. R. Coughlin. Molecular cloning of a functional thrombin receptor reveals a novel proteolytic mechanism of receptor activation. Cell. 64:1057–1068 1991).

Vu, T.-K. H., V. I. Wheaton, D. T. Hung, I. Charo, and S. R. Coughlin. Domains specifying thrombin-receptor interaction. Nature 353: 674–677 (1991).

Walz, D. A., G. F. Anderson, and J. W. Fenton. Responses of aortic smooth muscle to thrombin and thrombin analogues. Annals New York Acad. Sci. 485: 323–334 (1986).

White, R. P., Y. Shirasawa, and J. T. Robertson. Comparison of responses elicited by alpha-thrombin in isolated canine basilar, coronary, mesenteric, and renal arteries. Blood Vessels. 21: 12–22 (1984).

White, R. P., C. E. Chapleau, M. Dugdale, and J. T. Robertson. Cerebral arterial contractions induced by human and bovine thrombin. Stroke 11: 363–368 (1980).

Yang, S.-G., M. Saifeddine, A. Laniyonu, and M. D. Hollenberg. Distinct signal transduction pathways for angiotensin-II in guinea pig gastric smooth muscle: Differential blockage by indomethacin and tryosine kinase inhibitors. J. Pharmacol. Exp. Ther. 264: 958–966 (1992).

Yang. S.-G., A. A. Laniyonu, M. Saifeddine, G. J. Moore, and M. D. Hollenberg. Actions of thrombin and thrombin receptor peptide analogues in gastric and aortic smooth muscle: Development of bioassays for structure-activity studies. Life Sciences, 51: 1325–1332 (1992).

Zhong, C., D. J. Hayner, M. A. Corson, and M. S. Runge. Molecular cloning of the rat vascular smooth muscle thrombin receptor. J. Biol. Chem. 267: 16975–16979 (1992).

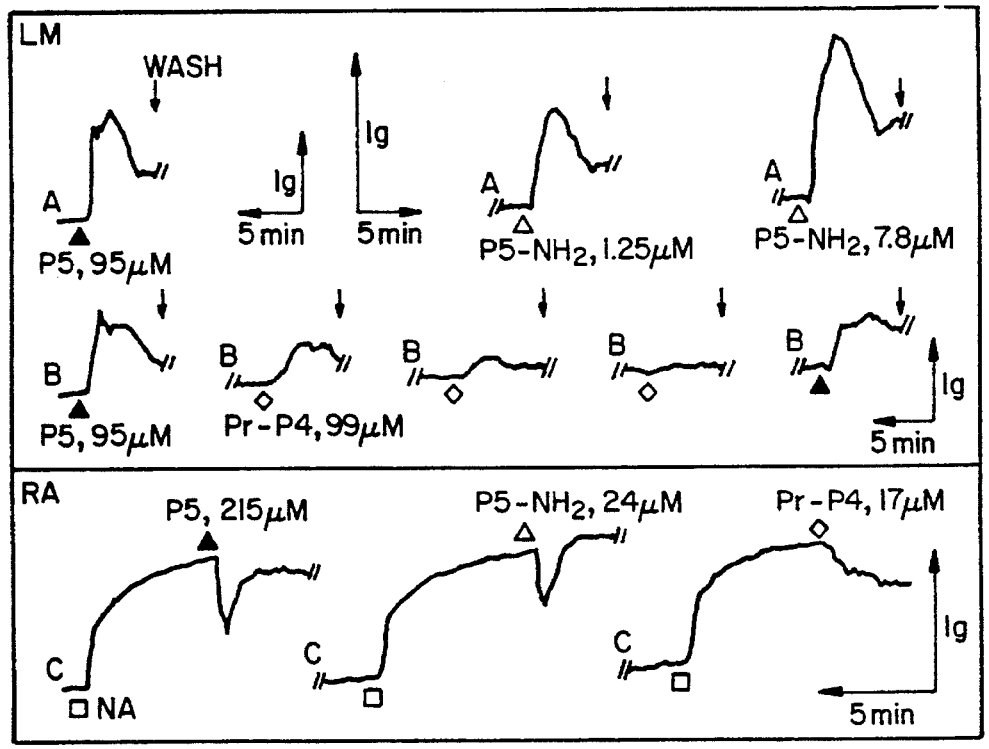
FIG_1
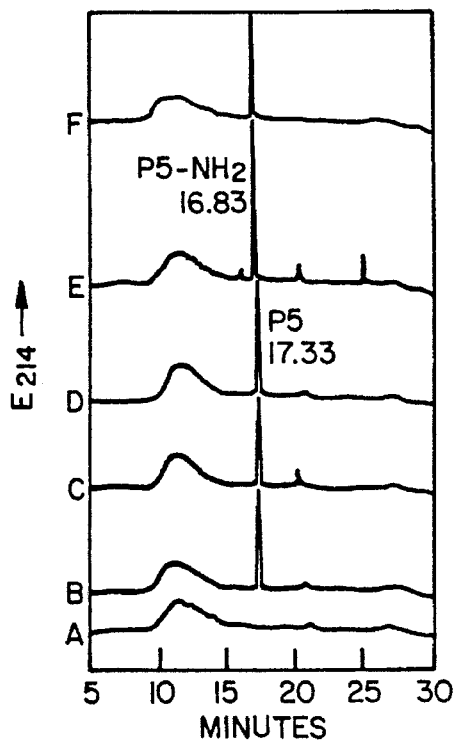
FIG_4

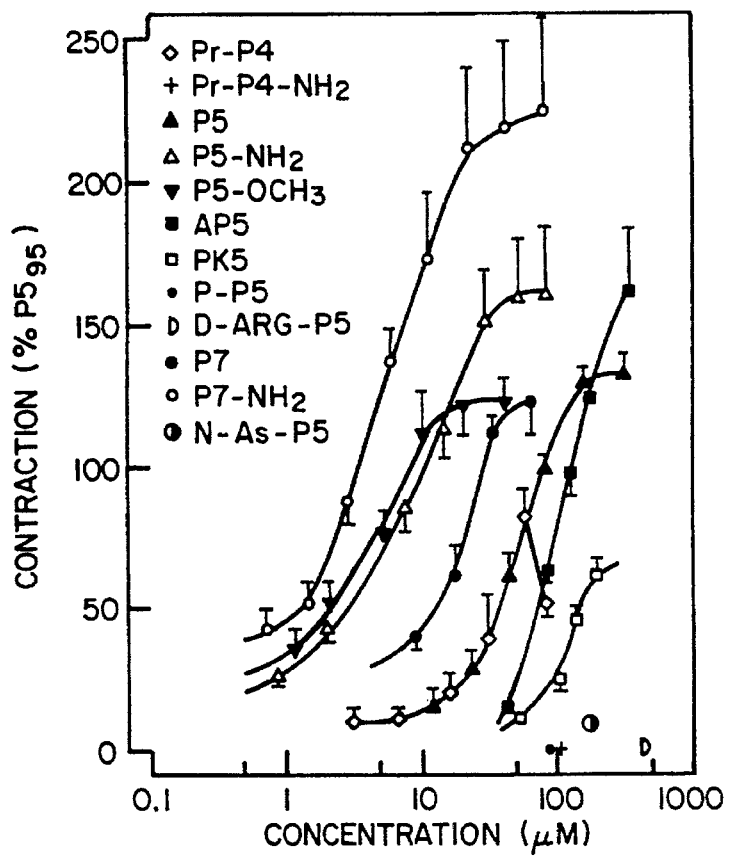
FIG_2A
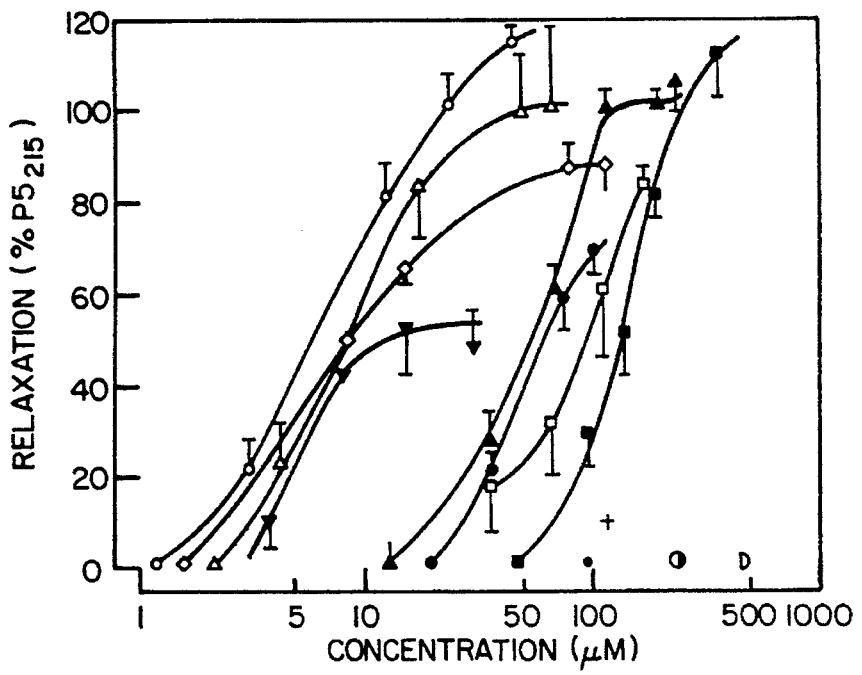
FIG_2B

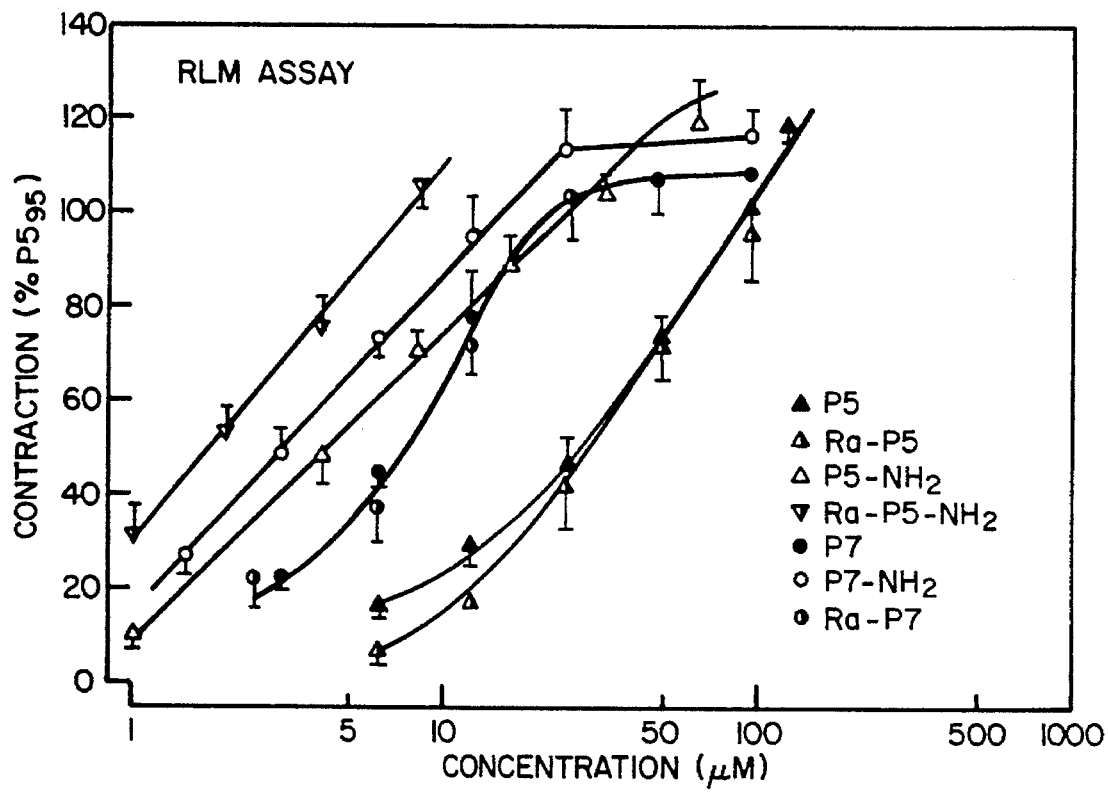
FIG_3A
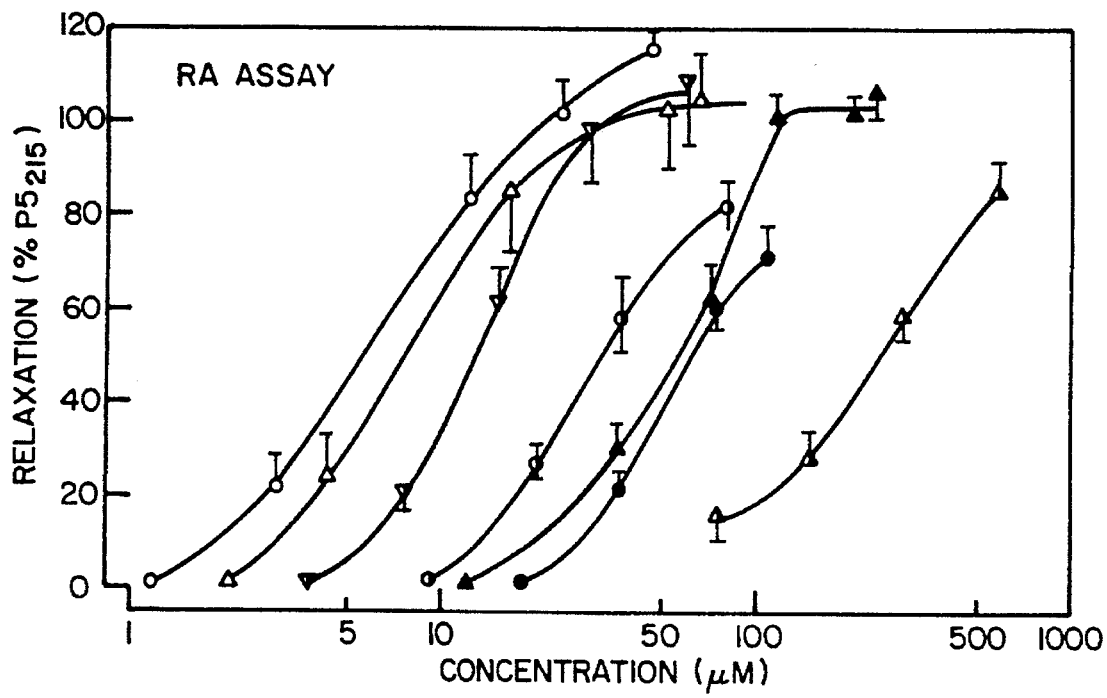
FIG_3B

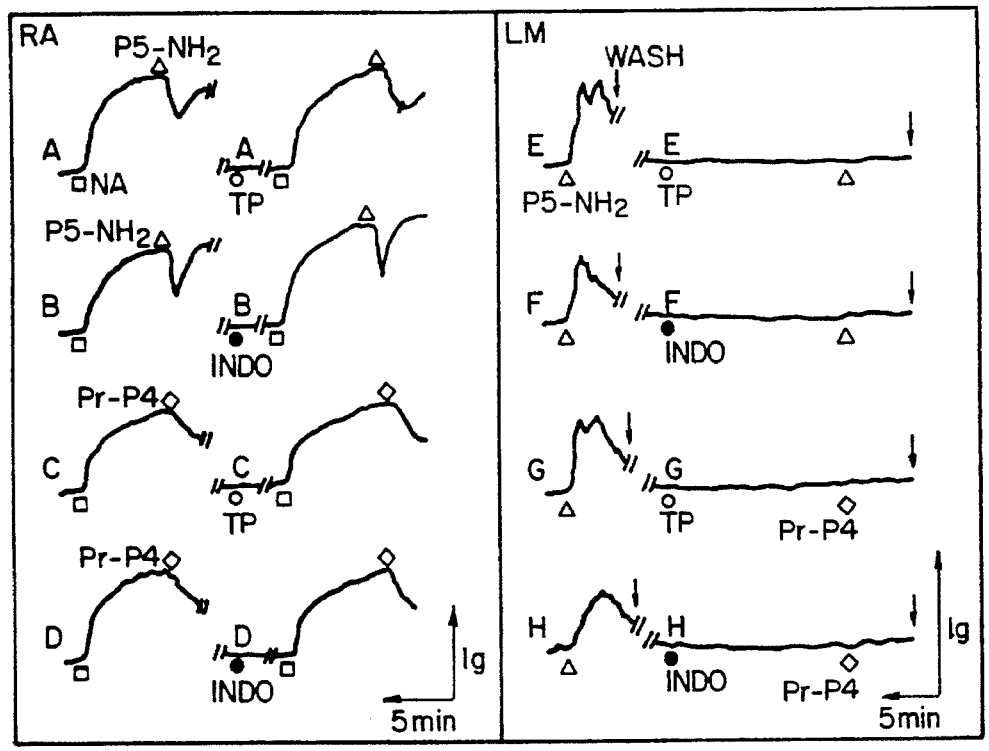
FIG_5
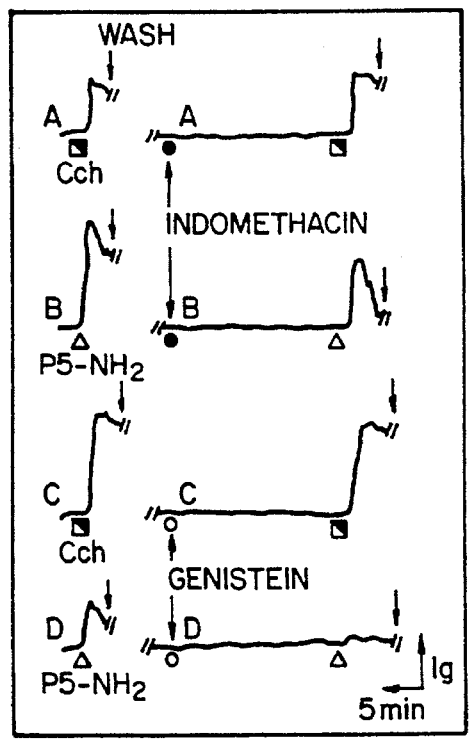
FIG_6

SYNTHETIC THROMBIN RECEPTOR PEPTIDES

This application is a continuation, of application Ser. No. 08/080,643, filed Jun. 21, 1993 now abandoned.

BACKGROUND OF THE INVENTION

1. Field of the Invention

This invention relates to materials involved the control of the cardiovascular systems, and in particular, to activities mediated by thrombin and its cellular receptor.

2. References

The following references are cited in this application as superscript numbers at the relevant portion of the application:

1. Vu, T.-K. H., D. T. Hung, V. I. Wheaton, and S. R. Coughlin. Molecular cloning of a functional thrombin receptor reveals a novel proteolytic mechanism of receptor activation. Cell. 64: 1057–1068 (1991).
2. Coughlin, S. R., T.-K. Vu, D. T. Hung, and V. I. Wheaton. Characterization of a functional thrombin receptor. J. Clin. Invest. 89: 351–355 (1992).
3. Vouret-Craviari, V., E. Van Obberghen-Schilling, U. B. Rasmussen, A. Pavirani, J.-P. Lecocq, and J. Pouyssegur. Synthetic α-thrombin receptor peptides activate G-protein-coupled signaling pathways but are unable to induce mitogenesis. Mol. Biol. Cell. 3:95–102 (1992).
4. Zhong, C., D. J. Hayner, M. A. Corson, and M. S. Runge. Molecular cloning of the rat vascular smooth muscle thrombin receptor. J. Biol. Chem. 267: 16975–16979 (1992).
5. Muramatsu, I., A. Laniyonu, G. J. Moore, and M. D. Hollenberg. Vascular actions of thrombin receptor peptide. Can. J. Physiol. Pharmacol. 70: 996–1003 (1992).
6. deblois, D., G. Drapeau, E. Petitclerc, and Marceau, Francois. Synergism between the contractile effect of epidermal growth factor and that of des-Arg$_9$-bradykinin or of α-thrombin in rabbit aortic rings. Brit. J. Pharmacol. 105: 959–967 (1992).
7. Vassallo, R. R., Jr., T. Kieber-Emmons, K. Cichowski, and L. F. Brass. Structure-function relationships in the activation of platelet thrombin receptors by receptor derived peptides. J. Biol. Chem. 267: 6081–6085 (1992).
8. Chao, B. H., S. Kalkunte, J. M. Maraganore, and S. R. Stone. Essential groups in synthetic agonist peptides for activation of the platelet thrombin receptor. Biochemistry 31: 6175–6178 (1992).
9. White, R. P., C. E. Chapleau, M. Dugdale, and J. T. Robertson. Cerebral arterial contractions induced by human and bovine thrombin. Stroke 11: 363–368 (1980).
10. DeMey, J. G., M. Claeys, and P. M. Vanhoutte. Endothelium-dependent inhibitory effects of acetylcholine, adenosine triphosphate, thrombin and arachidonic acid in the canine femoral artery. J. Pharmacol. Exp. Ther. 222: 166–173 (1982).
11. Rapoport, R. M., M. B. Draznin, and F. Murad. Mechanisms of adenosine triphosphate-, thrombin-, and trypsin-induced relaxation of rat thoracic aorta. Cir. Res. 55:468–479 (1984).
12. White, R. P., Y. Shirasawa, and J. T. Robertson. Comparison of responses elicited by alpha-thrombin in isolated canine basilar, coronary, mesenteric, and renal arteries. Blood Vessels. 21: 12–22 (1984).
13. Walz, D. A., G. F. Anderson, and J. W. Fenton. Responses of aortic smooth muscle to thrombin and thrombin analogues. Annals New York Acad. Sci. 485: 323–334 (1986).
14. Hollenberg, M. D., S. -G. Yang, A. A. Laniyonu, G. J. Moore, and M. Saifeddine. Action of thrombin receptor polypeptide in gastric smooth muscle: Identification of a core pentapeptide retaining full thrombin-mimetic intrinsic activity. Mol. Pharmacol. 42: 186–191 (1992).
15. Yang, S.-G., A. A. Laniyonu, M. Saifeddine, G. J. Moore, and M. D. Hollenberg. Actions of thrombin and thrombin receptor peptide analogues in gastric and aortic smooth muscle: Development of bioassays for structure-activity studies. Life Sciences, 51: 1325–1332 (1992).
16. Matsoukas, J. M., M. H. Goghari, M. N. Scanlon, K. J. Franklin, and G. J. Moore. Synthesis and biological activities of analogs of angiotensin II and III containing O-methyl-tyrosine and D-tryptophan. J. Med. Chem. 28: 780–783 (1985).
17. Vu, T.-K. H., V. I. Wheaton, D. T. Hung, I. Charo, and S. R. Coughlin. Domains specifying thrombin-receptor interaction. Nature 353: 674–677 (1991).
18. Yang, S.-G., M. Saifeddine, A. Laniyonu, and M. D. Hollenberg. Distinct signal transduction pathways for angiotensin-II in guinea pig gastric smooth muscle: Differential blockage by indomethacin and tyrosine kinase inhibitors. J. Pharmacol. Exp. Ther. 264: 958–966, 1992.
19. Muramatsu, I., H. Itoh, K. Lederis, and M. D. Hollenberg. Distinctive actions of epidermal growth factor-urogastrone in isolated smooth muscle preparations from guinea pig stomach: differential inhibition by indomethacin. J. Pharmacol. Exp. Ther. 245: 625–631 (1988).
20. Savarese, T. M., and C. M. Fraser. In vitro mutagenesis and the search for structure function relationships among G protein-coupled receptors. Biochem. J. 283: 1–19 (1992).
21. Dimaio, J., F. R. Ahmed, P. Schiller, and B. Belleau. Stereoelectronic control and decontrol of the opiate receptor. Recent Advances in Receptor Chemistry; F. Gualtieri, M. Giannella and C. Melchiorre, eds. 1979 Elsevier/North-Holland Biomedical Press. pp. 221–234 (1979).
22. Ahlquist, R. P. A study of the adrenotropic receptors. Amer. J. Physiol. 153: 586–600 (1948).
23. Barlos K., Gatos, D., Hondrelis, J., Matsoukas, J. M., Moore, G. J., Schafer, W. and Sotiriou, P. Preparation of new acid labile resins of the secondary alcohol type and their application in peptide synthesis. *Liebigs Ann. Chem.* 951–955 (1989).
24. Matsoukas, J. M., Agelis, G., Hondrelis, J., Yamdagni, R., Wu, Q., Ganter, R., Smith, J., Moore, D. and Moore, G. J. Synthesis and biological activities of angiotensin II, sarilesin and sarmesin analogues containing Aze or Pip at position 7. J. Med. Chem. 36: 904–911 (1993).
25. Matsoukas, J. M., Cordopatis, P., Belte, U., Goghari, M. N., Franklin, K. J. and Moore, G. J. Importance of the N-terminal domain of the type II angiotensin antagonist Sarmesin for receptor blockade. *J. Med. Chem.* 31: 1418–1421–(1988).
26. Stewart, J. M. and Young, J. D. Solid Phase Peptide Synthesis, Second Edition. Pierce Chemical Company, Rockford, Ill. (1984).

The disclosure of all publications, patents and patent applications are herein incorporated by reference in their entirety.

3. State of The Art Thrombin is a powerful factor in regulating the state of the cardiovascular system. It is clear that thrombin aids in the formation of blood clots by catalyzing the conversion of fibrinogen to fibrin, which is an integral part of most clots. In addition, thrombin is known to act directly on cells in the blood and on the interior blood vessel wall, and specifically to activate platelets to form clots. Thrombin-induced platelet activation is particularly important for arterial thrombus formation, a process that causes myocardial infarction and some forms of unstable angina and stroke. In addition, thrombin promotes inflammation and other cellular activities. Thrombin is chemotactic for monocytes, mitogenic for lymphocytes and smooth muscle cells, and causes endothelial cells to express the neutrophil adhesive protein GMP-140 on their surfaces and inhibits the growth of these cells. Thrombin elicits platelet-derived growth factor from the endothelium and is mitogenic for mesenchymal cells.

In addition to its role as a coagulation factor, thrombin is now known to regulate cell function via the proteolytic activation of a specific G-protein-linked cell surface receptor [1-4]. The novel mechanism whereby thrombin activates a target cell involves the proteolytic exposure of an N-terminal sequence of the receptor; this revealed N-terminal domain (beginning with Serine $_{42}$ of the human receptor) is then believed to act as an "anchored" and "tethered" ligand that activates the receptor [2]. Remarkably, it has been demonstrated that a peptide comprising only the first 14 amino acids of the thrombin-revealed N-terminal sequence of the human receptor (abbreviated P14) can, on its own, activate the thrombin receptor, so as to mimic many of the cellular actions of thrombin in a variety of target tissues [1,3,5-8]. In our own work [5], we have established that the human thrombin receptor-derived tetradecapeptide (P14, S$_{42}$ FLLRNPND-KYEPF$_{55}$, SEQ ID NO: 1) possesses thrombin-mimetic activity in both vascular and non-vascular smooth muscle preparations. In accord with the actions of thrombin itself [9-13], we observed that P14 can cause either a direct contractile response to gastric or vascular smooth muscle [5,4] or an endothelium-dependent relaxation of selected vascular smooth muscle preparations, such as the one derived from rat aortic tissue [5].

We used the guinea pig and rat gastric longitudinal muscle (LM) strip contractile assays [15] and the rat aortic (RA) ring relaxation assay as reliable and convenient bioassays to establish that only the first five amino acids of P14 (i.e., P5, or S$_{42}$FLLR$_{46}$, SEQ ID NO: 2) are required to mimic the actions of thrombin on smooth muscle preparations.[14] In the pentapeptide (S$_{42}$FLLR$_{46}$, SEQ ID NO: 2), we observed further that the C-terminal arginine-46 as well as phenylalanine-43 play critical roles in activating the thrombin receptor in the LM and RA tissues. The pentapeptide, P5, has also been shown to exhibit thrombin-like activity in fibroblasts [3] and in platelets [8]. Structure-activity studies have demonstrated that in platelets as well, the phenylalanine-43 and arginine-46 residues are important for the biological activity of the receptor-derived polypeptides [7,8].

There is a need for thrombin receptor activators and inhibitors having increased biological activity and/or resistance to degradation or metabolism.

SUMMARY OF THE INVENTION

This invention concerns novel peptides based on a thrombin receptor sequence and methods of synthesizing these novel peptides. Also disclosed are novel branched-chain copolymer compounds and derivatized solid supports containing these novel peptides or other peptides which are based on a thrombin receptor sequence.

These peptides and/or compounds may be used diagnostically and therapeutically.

In one aspect, the present invention provides peptides based on a thrombin receptor sequence comprising the amino acid sequence $X_1\psi X_2 X_3 \Omega X_4$ (SEQ ID NO: 3), wherein $\psi$ is selected from the group consisting of natural aromatic amino acids, non-natural aromatic amino acids, and derivatives of said natural or non-natural aromatic amino acids; $\Omega$ is selected from the group consisting of natural basic amino acids, non-natural basic amino acids, and derivatives of said natural or non-natural basic amino acids; $X_1$ is selected from the group consisting of —H, natural amino acids, non-natural amino acids, derivatives of said natural or non-natural amino acids, acyls of from 1 to about 3 carbon atoms, alkyls of from 1 to about 5 carbon atoms, aryls, and alkylaryls; $X_2$ and $X_3$ are, independently, selected from the group consisting of no amino acid residue, natural amino acids, non-natural amino acids, and derivatives of said natural or non-natural amino acids; and $X_4$ is selected from the group consisting of —B(OH)$_2$, —H, natural amino acids, non-natural amino acid, derivatives of said natural or non-natural amino acids, and substituent groups which block carboxypeptidase.

In another aspect, the present invention provides peptide-containing compounds comprising $X_6$—$X_7$—$X_8$, wherein $X_6$ and $X_8$ are each, independently, a peptide according to claim 1 or 22, $X_7$ is a hydrophilic spacer arm, and $X_6$ and $X_8$ are each joined to $X_7$ at a site selected from the group consisting of the C-terminus when $X_6$ or $X_8$ is a linear peptide and a side chain when $X_6$ or $X_8$ is a cyclic peptide. Peptide-containing compounds comprising:

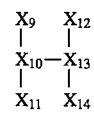

wherein $X_9$, $X_{11}$, $X_{12}$, and $X_{14}$ are each, independently, a peptide according to claim 1 or 22; $X_{10}$ and $X_{13}$ are each a hydrophilic spacer arm; $X_9$ and $X_{11}$ are each joined to $X_{10}$ at a site selected from the group consisting of the C-terminus when $X_9$ or $X_{11}$ is a linear peptide and a side chain when $X_9$ or $X_{11}$ is a cyclic peptide; and $X_{12}$ and $X_{14}$ are each joined to $X_{13}$ at a site selected from the group consisting of the C-terminus when $X_{12}$ or $X_{14}$ is a linear peptide and a side chain when $X_{12}$ or $X_{14}$ is a cyclic peptide are also provided.

In a further aspect, the present invention provides cyclic peptides based on a thrombin receptor sequence. Methods for making such cyclic peptides are also provided.

In some of its method aspects, the present invention provides methods for treating cardiovascular disease, treating inflammatory disease, accelerating wound healing, decreasing scarring during wound healing, and preventing tumor angiogenesis and/or metastasis comprising administering to a subject in need of such treatment an effective amount of at least one peptide or compound based on a thrombin receptor sequence.

In a yet further aspect, the present invention provides solid supports comprising at least one peptide or compound based on a thrombin receptor sequence.

BRIEF DESCRIPTION OF THE DRAWINGS

FIG. 1 illustrates the response of the guinea pig longitudinal muscle (GLM) and rat aorta (RA) assays to TRP analogues.

FIG. 2 illustrates concentration-effect curves for TRP analogues in the GLM and RA assays.

FIG. 3 illustrates contraction-effect curves for TRP analogues in the rat gastric longitudinal muscle (RLM) and RA assays.

FIG. 4 illustrates the chromatographic analysis of P5 and P5-$NH_2$ recovered from the RLM and RA assay media.

FIG. 5 illustrates the effects of tyrphostin and indomethacin on the actions of P5-$NH_2$ and Pr-P4 in the RA and GLM assays.

FIG. 6 illustrates the effects of genistein and indomethacin on the actions of P5-$NH_2$ and carbachol in the RLM assay.

DETAILED DESCRIPTION OF THE INVENTION

1. Definitions

As used above, and throughout this specification, including the description of this invention, the following terms, unless otherwise indicated shall be understood to have the following meanings:

"Thrombin receptor sequence" means the five amino acid N-terminal domain, beginning with Serine of the human G-protein-linked cell surface receptor.

"Natural amino acid" means an amino acid found in nature.

"Non-natural amino acid" means a synthetic amino acid not found in nature.

"Derivative of an amino acid" means a modified natural or non-natural amino acid.

"Cyclic peptide" means peptides wherein each amino acid residue is attached at both its C-terminus and its N-terminus to another amino acid residue or spacer group.

2. Nomenclature

The following abbreviations have the following meanings when used in this application:

Aca (or Acp): ε-Amino Caproic Acid
DMF: Dimethylformamide
DCM: dichloromethane
IPrOH: isopropanol
MeOH: Methanol
$Et_2O$: diethylether
n-BuOH: Butanol
AcOH: Acetic Acid
TRP: thrombin receptor-derived peptides
tBu: t-butylester
Tos: p-Toluenesulfonyl (Tosyl)
PMC: 2,2,5,7,8-pentamethyl-chroman-6-sulfoxyl
FMOC or Fmoc: 9-Fluorenyl-methoxycarbonyl
R: 2-chlorotriphylmethyl (trityl) resin
DIPEA: Diisopropylethylamine
DCC: N-N'dicyclohexylcarbodiimide
TFA: Trifluoroacetic acid
TFE: Trifluoroethanol
HOBt: 1-Hydroxy Benzotriazole
GLM: Guinea pig longitudinal muscle assay
RLM: Rat gastric longitudinal muscle assay
LM: Either or both GLM and RLM
RA: Rat aorta assay If an abbreviation is used which has not been previously defined, either above or parenthetically, it is to be taken as having the standard meaning known in the art.

The nomenclature used to describe the peptide compounds of the invention follows the conventional practice where the N-terminal amino group is assumed to be to the left and the carboxy group to the right of each amino acid residue in the peptide. In the formulas representing selected specific embodiments of the present invention, the amino- and carboxy-terminal groups, although often not specifically shown, will be understood to be in the form they would assume at physiological pH values, unless otherwise specified. Thus, the N-terminal $H^+_2$ and C-terminal $O^-$ at physiological pH are understood to be present though not necessarily specified and shown, either in specific examples or in generic formulas. Free functional groups on the side of the amino acid residues can also be modified by amidation, acylation or other substitution, which can, for example, change the solubility of the compounds without affecting their activity.

In the peptides shown, each amino acid residue is represented by a single letter designation, corresponding to the trivial name of the amino acid, in accordance with the following conventional list:

| Amino Acid | 1 Letter Symbol | 3 Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Following conventional practice, the use of the lower case one letter symbol for an amino acid denotes the D-form of that amino acid. If not otherwise specified, the term amino acid, whether natural or non-natural, includes both D- and L-forms.

The abbreviations for some amino acids not naturally occurring are indicated in the discussion below. Certain commonly encountered amino acids, which are not naturally occurring, include, for example, beta-alanine (beta-Ala or bAla), or other omega-amino acids, such as 3-amino propionic, 4-amino butyric (4 Abu) and so forth, alpha-aminisobutyric acid (Aib), sarcosine (Sar or MeGly), ornithine (Orn), citrulline (Cit), t-butylalanine (t-BuA), t-butylglycine (t-BuG), N-methylisoleucine (N-MeIle or MeIle), phenylglycine (Phg), and cyclohexylalanine (Cha), norleucine (Nle), cysteic acid (Cya), 2-naphthylalanine (2-Nal), 1,2,3,4-tetrahydroisoquinoline-3-carboxylic acid (Tic), β-2-thienylalanine (Thi), methionine sulfoxide (MSO), hydroxyproline (HyPro, 3 Hyp or 4 Hyp), L-azetidine-2-carboxylic acid (Aze), and L-pipecholic acid (Pip).

Other amino acid substitutions can also be included in peptide compounds within the scope of the invention.

All of the compounds of the invention, when an amino acid forms the C-terminus, may be in the form of the pharmaceutically acceptable salts or esters. Salts may be, for example, $Na^+$, $K^+$, $Ca^{+2}$, $Mg^{+2}$ and the like; the esters are generally those of alcohols of 1-6 C.

3. Synthesis

The synthesis of linear peptides may be accomplished by methods well-known to one skilled in the art. For example, compounds can be synthesized by the solid phase method using one or more strategies known to one skilled in the art, such as those disclosed generally in J. Stewart and J. Young, *Solid Phase Peptide Synthesis*, 2nd Ed. (1984), Pierce Chemical Co. or as disclosed previously by our own laboratory [16].

In general, the peptides synthesized for use in the present invention were released from the resin, deprotected with anhydrous HF (the Boc strategy) or TFA (the Fmoc strategy), then purified to homogeneity (i.e. a single peak) using reversed phase high performance liquid chromatography (HPLC). Peptide compositions were confirmed by amino acid analysis and, where appropriate, by mass spectral analysis.

In the novel solid phase peptide synthesis method described in the present invention, synthesis is carried out at room temperature. The resin is a novel chloro-(orthochloro)-trityl-resin to which the FMOC-protected, terminal amino acid is attached in the presence of diethylpropylamine (1.1 equivalents) in methylene chloride for 1 hour. The formula of the resin is as follows:

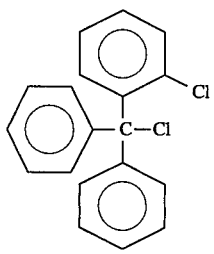

Traditionally, two solid phase peptide synthesis strategies using Boc-amino acids and FMOC-amino acids, respectively, have been used [25, 26]. In the BOC strategy, the peptide-resin bond is cleaved with the use of strong acid conditions, such as anhydrous HF, such that the protecting groups are simultaneously removed. In the FMOC-strategy, the peptide-resin is cleaved with the use of intermediate acid conditions, such as TFA, so that most or all of the protecting groups are also simultaneously removed. Using the novel (orthochloro) trityl resin [23] the condition for cleaving the peptide-resin bond is so mild that even the most acid-sensitive protecting groups commonly used in solid phase peptide synthesis remain attached to the peptide. Consequently, the ability to retain the acid-sensitive protecting groups has thus allowed the present inventors to synthesize new and useful analogues of biologically active ligands such as gonadotrophin releasing hormone, opiate peptides and angiotensin-II [24] as well as both linear and cyclic thrombin receptor-derived peptides (TRPs).

Using the (orthochloro) trityl resin [23], stepwise synthesis of the peptide with FMOC-amino acids (2.5 equivalents) is achieved with DCC/HBT (2.5 equivalents) as coupling agent(s) in a suitable solvent such as DMF for 1–2 hours, and the FMOC groups are removed by treatment with 20% piperidine in DMF for 10–30 minutes. Acid-sensitive side chain protecting groups such as, t-butyl for Ser, PMC for Arg, Boc for Lys, and the like, remain intact when the peptide-resin bond is cleaved with trifluoromethanol/acetic acid/methylene chloride in a ratio of 7:1:2, respectively. See Table 1 for details of synthesis parameters.

TABLE 1

Solid phase peptide synthesis of linear
SFLLR (SEQ. ID NO: 2), FLLR (SEQ. ID NO: 4), SFLLR-AC
(SEQ. ID NO: 5), FLLR-AC (SEQ. ID NO: 6) using $N^\alpha$-Fmoc
amino acids and 2-chlorotritylchloride resin a,b,c,

| Procedure | Reagents/Solvents | Vol. (ml) | Time (min) |
|---|---|---|---|
| Washing (3×) | Dimethylformamide (DMF) | 10 | 2 |
| Fmoc-deprotect | 20% Piperidine in DMF | 10 | 30 |
| Washing (3×) | Dimethylformamide | 10 | 2 |
| Washing (3×) | 2-Propanol | 10 | 2 |
| Washing (2×) | Diethylether (KAISER TEST) | 10 | 2 |
| Washing (3×) | Dimethylformamide | 10 | 2 |
| Coupling$^c$ | 2.5 equiv. Fmoc-Amino acid, 3.75 equiv. HOBt and 2.75 equiv.DCC in 4 ml Dimethylformamide | 10 | OVER-NIGHT |
| Washing (3×) | Dimethylformamide | 10 | 2 |
| WaBhing (3×) | 2-Propanol | 10 | 2 |
| Washing (3×) | Dimethylformamide | 10 | 2 |
| Washing (3×) | 2-Propanol | 10 | 2 |
| Washing (2×) | Diethylether (KAISER TEST) | 10 | 2 |

$^c$Quantities are relative to 1 g of resin. A 0.5 equiv of Fmoc-protected amino acid was dissolved in the minimum quantum of DMF (1–2 ml) and stirred for 10 min in a 25 ml round bottom flask at 0° C.. Then 3.75 equivalent of HOBt and 2.75 equivalent of DCC dissolved in DMF was added and the mixture was stirred for another 20 min at 0° C. and 10 min at room temperature. The mixture was filtered directly into the reaction vessel and the reaction mixture was stirred for 16 h. Solid phase peptide synthesis was carried out using a manually handled reaction vessel (2 × 12 cm) equipped with a porous G filter (size 2) and tapattle bottom connected with a water aspirator. A vibrator was used shaking the reaction vessel throughout the several steps. Completion of deprotection of coupling was identified by the ninhydrin test (KAISER TEST). A second coupling under the same conditions was employed in cases of incomplete coupling.

Our novel finding for the synthesis of cyclic TRP analogues is that the synthesis should be initiated using a substituent (Aca) or an amino acid (e.g. FMOC-Leu—OH) other than arginine as the very first amino acid to be attached on the resin (e.g. see Schemes I, II, III, and IV). Conventional attachment of the last amino acid Arg of the peptide sequence SFLLR (SEQ ID NO: 2) to the resin, will not allow cyclization of the linear peptide after its removal from the resin due to steric hindrance. The initial step is critical when preparing cyclic analogues of the TRP $_{42\text{-}46}$ sequence; otherwise their synthesis will fail.

Cyclization of the linear peptide Leu-Arg-X-Ser-Phe-Leu (X=no residue, Gly, Aca, Lys, etc.) (SEQ ID NO: 2), in which the acid-sensitive side chain protecting groups, t-butyl (Ser), PMC (Arg) and Boc (Lys) remain intact, will take place using DIPEA as a base and the BOP reagent as cyclization agent, in DMF solution. The cyclization process is easily monitored by the ninhydrin test of the synthesized peptide resolved by thin layer chromatography using $CHCl_3$: MEOH (6:1) as a solvent system. Successfully cyclized products are ninhydrin negative. The protected cyclic peptide is then treated with 60% TFA in dichloromethane for two hours and the final free cyclic TRP $_{42\text{-}46}$ peptide is recovered after precipitation with ether. The final product is purified further by HPLC.

The novel compounds produced according to the unique procedures described above are cyclic analogues of TRP $_{42\text{-}46}$ in which an FMOC-Leu—OH is the first amino acid to be used for initiating the linear peptide sequence, which subsequently is cyclized and for which acid-sensitive protecting groups are maintained up to the end of the synthesis as a result of the use of an extremely labile peptide-resin bond provided by the (orthochloro) trityl-resin bond. Such analogues include, but are not limited to, compounds having the Formula III.

Solid phase synthesis and polymerization of multimer TRP compounds may be accomplished using related methods. This method for making active branched chain polymers of TRPs is not limited to, but exemplified by peptide-containing compounds where two or more TRPs, including cyclic TRPs, are joined via an appropriate spacer arm such as, for example, a hydrophilic spacer arm. The link to the spacer arm is at the C-terminus of each TRP. Thus, one may form multimers via side chains included in the cyclic peptide structure. The novelty of the proposed method lies in using the (orthochloro) trityl resin from which synthetic peptides can be released, so as to retain all of the side-chain protecting groups, leaving a free peptide carboxyl for subsequent cross-linking reactions. In the case of cyclic TRPs, an appropriate side-chain for coupling can be incorporated into the structure, according to the method previously described. The general scheme for the synthesis of one such multidentate compound is outlined in Scheme V.

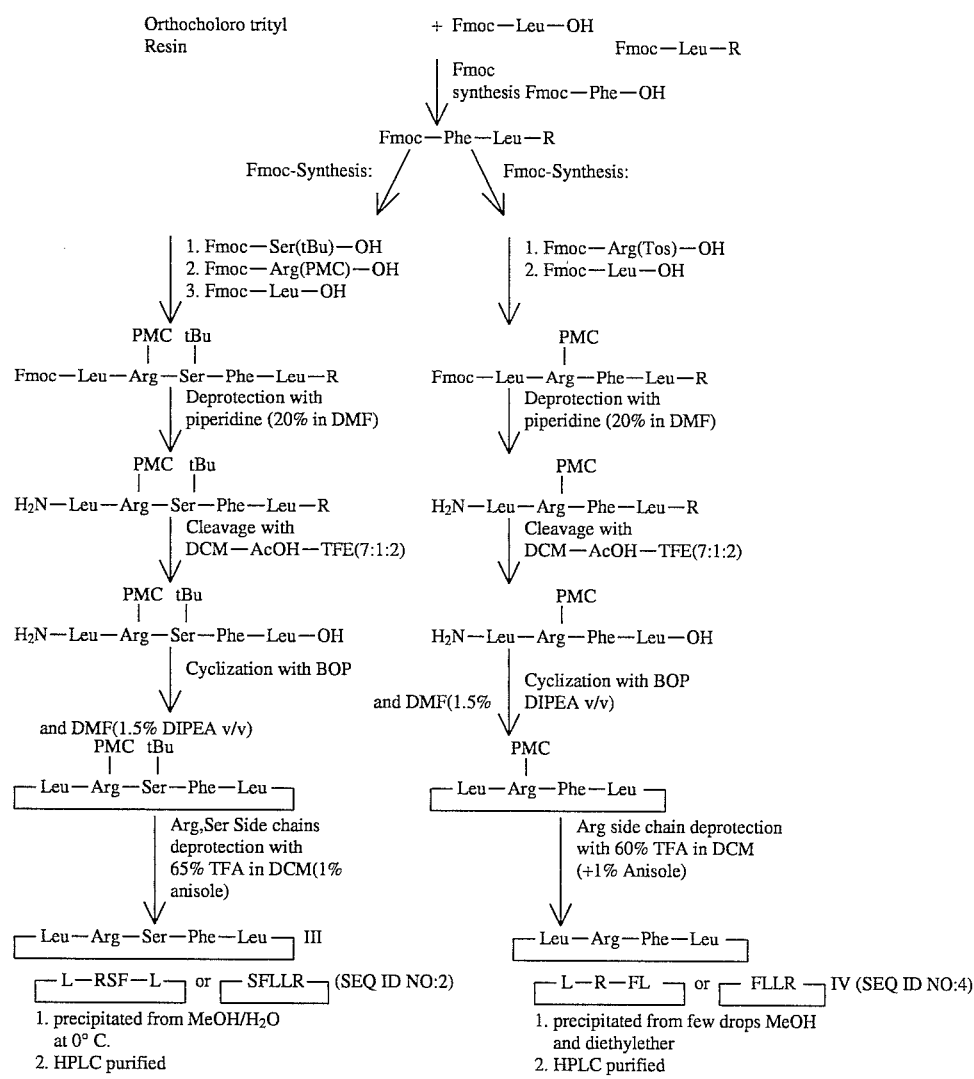

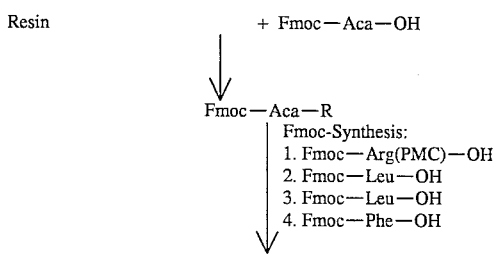

-continued
SCHEME II
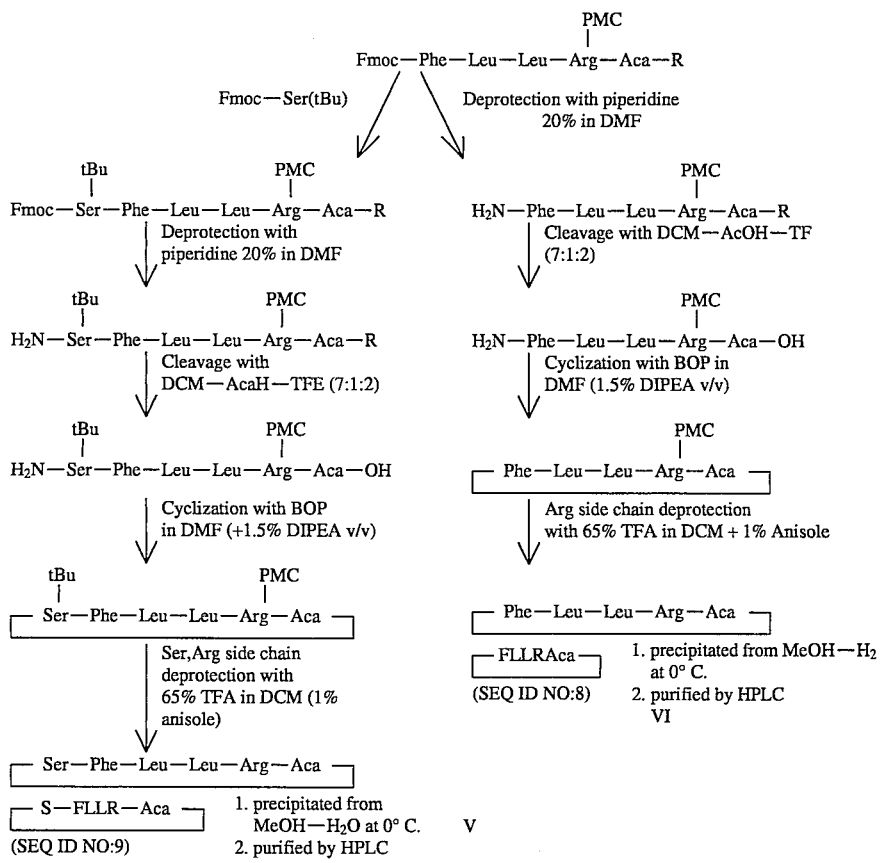
SCHEME III
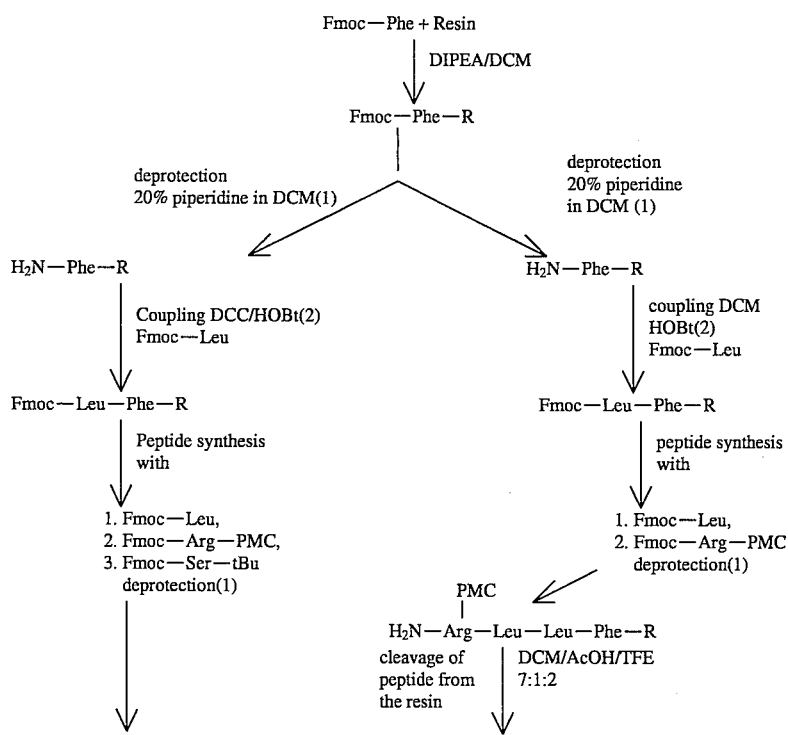

-continued
SCHEME III
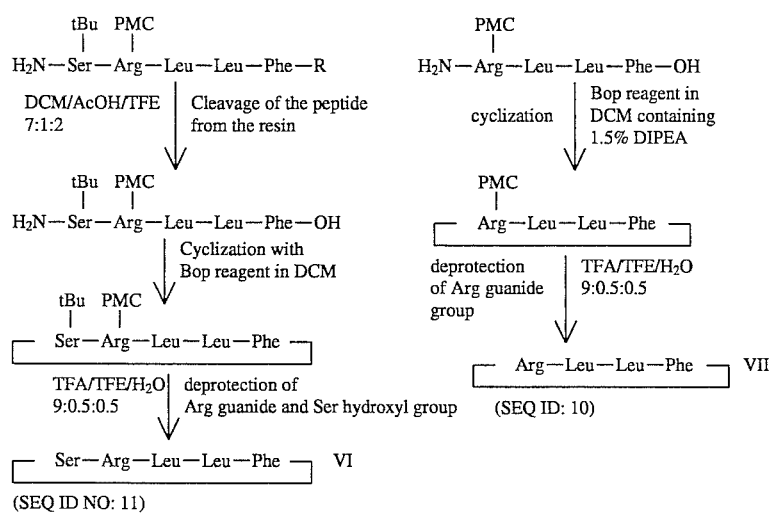
SCHEME IV
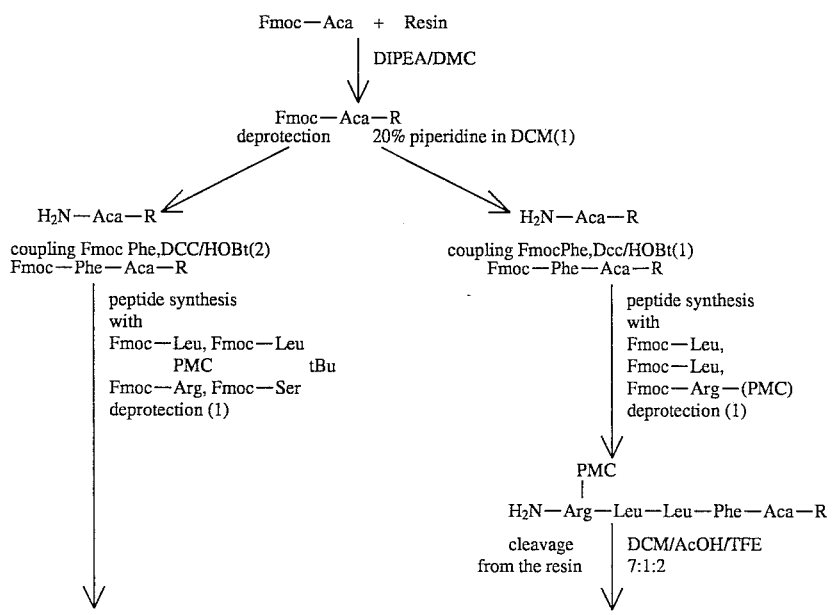

-continued
SCHEME IV

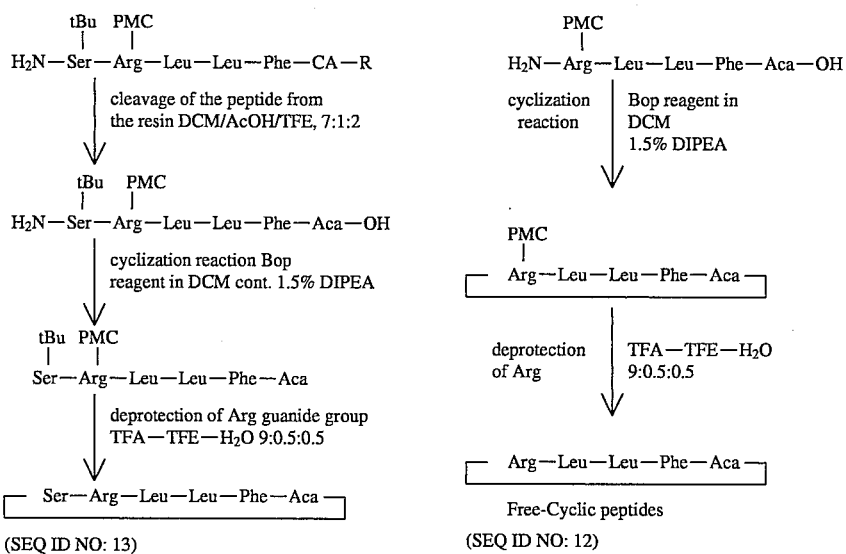

(SEQ ID NO: 13)     (SEQ ID NO: 12)

SCHEME V

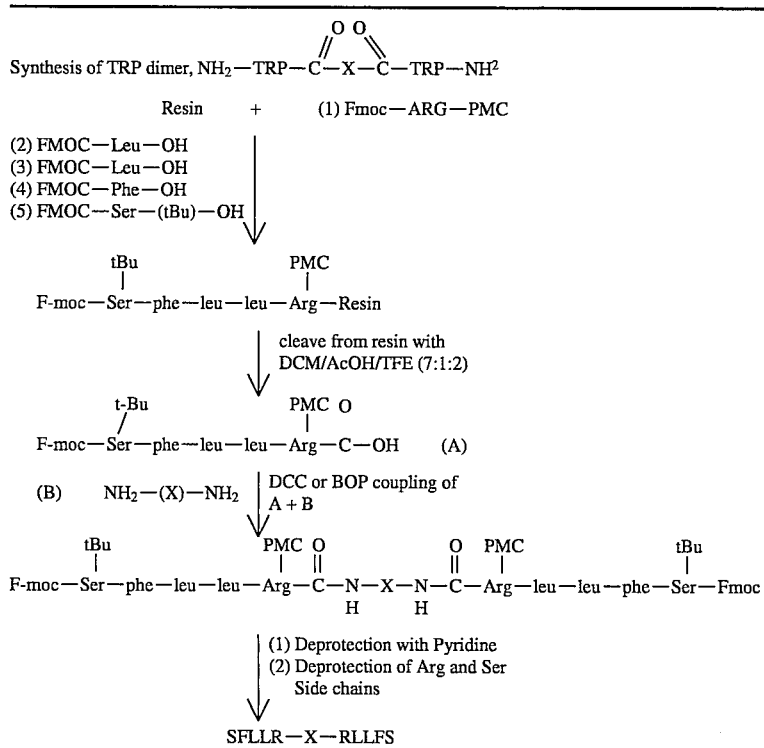

Where X is a hydrophilic spacer arm or other linking group, including an insoluable inert polymer.

The peptides and multimer TRP compounds of the present invention may also be immobilized or derivatized onto solid supports using conventional methods. Such solid supports may include degradable implants, bandaids, gauze, polymers, membranes sepharose, cellulose, polyacrylamide particles, and the like. Such supports are either commercially available or can be prepared using conventional methodology.

The peptides, linear and cyclic, and multidentate TRP compounds of the present invention may be coupled to or derivatized onto a solid support by methods known in the art. The solid support may be appropriately functionalized so that complimentary reactive functionalities are employed on the solid support and the compound to be immobilized. For example, if an amine group is used as the surface reactive group on the solid support, then the functional group on the compound should be a group which is reactive with amine (e.g., a carboxylic acid).

Utility

In the structure-activity studies of the thrombin receptor-derived polypeptides (TRPs) done by us [14] and by others [7,8], we were struck by two principle observations: (1) The potency of the receptor-derived peptides first increased, upon shortening the peptide from fourteen ($TRP_{42-55}$) to six residues ($TRP_{42-47}$), followed by a marked reduction in potency upon shortening the hexapeptide further to a pentapeptide (P5, $TRP_{42-46}$) and then by an abrogation of activity upon shortening the peptide to the 4-mer, SFLL(SEQ ID NO: 14); and (2) Acetylation of the N-terminus abolished the activity of the otherwise active receptor-derived peptides. These data pointed to the key importance of the amino and carboxy-terminal regions of the pentapeptide for its intrinsic thrombinmimetic biological activity.

The peptides useful in the present invention are generally based on the sequence XFXXR(SEQ ID NO: 15), where X represents any naturally occurring for non-naturally occurring amino acid analogue, in either its D or L form. Additionally, F and R may be substituted with any natural or non-natural derivative that is aromatic in position 2 and that bears either a positive charge in position 5 or an atom or group, such as N, capable of forming a hydrogen bond. The residues at positions 2 and 5 may also incorporate fluorine or organic substituents that mimic the aromatic or basic substituents.

In addition, our data indicate that C-terminal extensions of these peptides will still be active. Thus, compounds based on the structure $H_2N$-XFXXR-$(1)_n$-$(2)_m$-RXXFS-$NH_2$ (with n and m, independently, equal to O or an integer from 1 to about 10) may be used. In this multimeric configuration, the linear TRP peptides are linked via their C-terminus to variable spacer arms (1) and (2). When the peptides used are cyclic peptides, they may be linked to the spacer arms via reactive side chain groups.

The spacer arm units (1) and (2) can be a variety of organic units, including peptides, polysaccharides, and polyamines. Each spacer arm unit may be linked to two or more linear or cyclic TRPs, as well as to the other spacer arm unit, to form branched co-polymers which comprise four or more peptide units. Polylysine may be particularly preferred for use in the present invention, as it can be linked to more than two peptides.

The use of this construction provides branching peptide multimers that may augment the potency of the monomeric peptides.

The present invention also includes cyclic peptides based on the thrombin receptor.

These include thrombin receptor pentapeptide or tetrapeptide cyclic derivatives in Class A as follows:

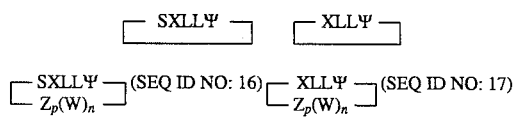

and thrombin receptor pentapeptide or tetrapeptide cyclic derivatives with reversed position of R and F in Class B, as follows:

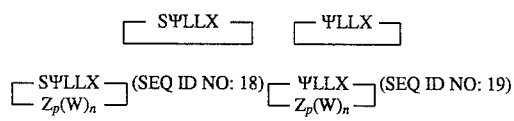

be made:
X=F, F(5Fluoro), Y, H, Cha, f
ψ=R, Lys, Orn, r
Z=any naturally occurring amino acid, non-naturally occurring amino acid analogue, or a hydrophilic spacer arm. (In a preferred embodiment, Z is Aca, Amino propanoic acid (AP), Amino butyric acid (AB), Amino pentanoic acid, or glycine.)
W=—OH, —$NH_2$, —COOH
n=0, 1, 2, 3, 4
and
p=0, or an integer from 1 to about 10.

Additionally, other included cyclic peptides are cyclic derivatives based on an F, R sequence in Class C as follows:

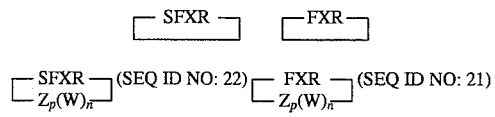

and cyclic derivatives based on an R,F sequence in Class D, as follows:

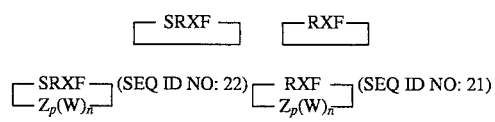

The following substitutions for classes C and D may be made:
X=Pro, HyPro, Aze, Pip, Sar
Z=any naturally occurring amino acid, non-naturally occurring amino acid analogue, or a hydrophilic spacer arm. (In a preferred embodiment, Z is Aca, Amino propanoic acid (AP), Amino butyric acid (AB), Amino pentanoic acid, or glycine.)
W=—OH, —$NH_2$, —COOH
n=0,1,2,3,4
p=0 or an integer from 1 to about 10.

Another class of cyclic peptides are Class E, as follows:

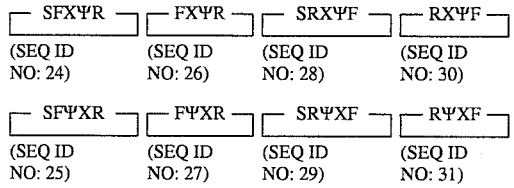

The following substitutions for class E may be made:
X=E(Glu), D(Asp)
ψ=K (Lys), Orn In each of these classes (A-E), W may also be CH—$NH_2$, in which case, Z may then be lys, orn, diamino-2,4-butyric acid or 2,3-diamino propionic acid.

The TRP linear and cyclic peptides and multimeric compounds of the present invention may be useful as agonist or antagonists in treating disorders where the thrombin receptor is involved, such as, but not limited to, cardiovascular disease, inflammatory disease, gastrointestinal disease, osteoporosis, tissue injury and repair (including nerve regeneration, both in the CNS and peripherally) and cancer in humans and the other animals.

They may also be used for laboratory diagnosis and thrombin-mimetic studies, as for example, in disorders of thrombin receptor function. TRPs may be used to study disorders or dysfunctions of platelets or white blood cells.

Thrombin receptor antagonists could prove of use in the setting of cardiovascular disease such as atherosclerosis and myocardial infarction from two perspectives. First, such antagonists will modulate platelet function and act synergistically with aspirin-related compounds that reduce platelet aggregation, thereby protecting against initial or repeat myocardial infarction, similar to the results obtained with other anti-platelet drugs. The thrombin receptor antagonists may also be useful in the setting of transient ischaemic attacks. Further, the anti-thrombin receptor drugs may be of use in the context of acute myocardial infarction, or other settings where a hypercoagulable state occurs. The thrombin receptor antagonist may be used to reduce thrombus formation and clot propagation either in the vicinity of damaged ventricular muscle or at the site of a pulmonary embolus. When present on solid supports, the agonists (or antagonists) may be used to attach to the surface of prostheses exposed to the blood to regulate the formation of clots or thrombi and to facilitate a healing process, thereby promoting the efficacy of an implanted prosthesis. Additionally, thrombin receptor antagonists may be used to retard the development of arterial plaque formation, wherein intimal vascular muscle hypertrophy and hyperplasia appears to play some role. The antagonist TRPs may be used in the setting of endarterectomy repair. The vascular endothelial cell, which is also thought to play a role in this process also is a target for the action of thrombin, and by extension, the receptor-related peptides. Since thrombin formation at such a site of vessel wall pathology likely plays a mitogenic role, the receptor antagonist would reverse such an action of thrombin both on the smooth muscle elements and on the endothelial cells.

At sites of inflammation, such as those present in arthritic joints, the liberation of proteases, which could readily activate the thrombin receptor, appears to play some role. Data in the literature suggest that the thrombin receptor could be activated by proteases other than thrombin. Therefore, one component of an inflammatory reaction could comprise the activation of a thrombin receptor. Thrombin itself can cause bone resorption; such an action would be of importance in the setting of deforming arthritis, osteoporosis, or in a situation where a bone implant causes bone resorption. Thrombin receptor antagonists may be used to examine the role of the thrombin receptor in the setting of inflammatory disease states. Further, these thrombin receptor antagonists could be used as anti-inflammatory drugs or to prevent osteoporosis.

In the setting of tissue injury and repair, such as a wound or a surgical incision it could be advantageous to accelerate the healing process. The acceleration of would healing would also prove of value in the use of skin grafts for treating burn patients and in treatment of ocular injuries. It is likely that thrombin itself, generated at the site of injury, plays an important role in directing the healing process. In most settings, one would wish to accelerate the healing process; alternatively, in some situations, one might wish to delay the healing process to avoid the formation of inappropriate scarring, leading to the formation of cheloid. Thus, for sites of injury and tissue repair, it could prove of use to have available both the thrombin receptor agonists and thrombin receptor antagonists, depending on the situation. A non-degradable super-active analogue of the thrombin receptor peptide may be preferably used for such treatment in both humans and animals. The agents may also be used in the therapy of duodenal, ileal and colonic ulcer disease, as well as in the setting of nerve cell degeneration.

In the setting of tumor formation, angiogenesis and metastasis are critical factors. Activation of the thrombin receptor in the vicinity of a developing tumor may play a role in both angiogenesis and metastasis. The production of extracellular proteases by tumor cells and the ability of such protease to activate the thrombin receptor could readily contribute to the pathophysiology of tumor spread and tumor vascularization. Apart from these immediate effects of the tumor, it is well-recognized that individuals with a tumor load can suffer from a hypercoagulable state and from disseminated intravascular coagulation. Thus, from the point of view of angiogenesis, metastasis and the distant effects of a tumor on a cancer patient, thrombin receptor antagonists are useful.

We had previously established using the GLM bioassay that the intrinsic activity of the revealed N-terminal sequence, beginning at residue 42 of the human receptor sequence, resides in the first five amino acids (i.e. P5, $S_{42}FLLR_{46}$,(SEQ ID NO: 2), wherein the phenylalanine$_{43}$ and arginine$_{46}$ appear to be the major pharmacophores. Within this sequence, the third residue (leucine in the human sequence; phenylalanine in the rodent sequence) has been shown to play a minor role. We have found that, although the P5 pentapeptide motif is sufficient for exhibiting thrombin-mimetic activity, the charge properties of the amino and carboxyterminal residues appear to play major roles in terms of the intrinsic activities of the TRPs in both the LM and RA receptor systems. The quantitative recovery of intact peptide from the RA and LM organ baths (FIG. 4) appear to rule out peptide metabolism as playing a major role in determining the relative potencies of the agonists we have studied. From the observations with P5, Ra-P5, P5-NH$_2$, Ra-P5-NH$_2$, P7, and P7-NH$_2$ in GLM, RLM and RA systems, we have found that removing the negative charge of the C-terminal residue of the TRPs by amidation or esterification results in a marked increase in potency (about 10-fold). From these data, one may suggest, without being bound to any theory, that the absence of a C-terminal carboxyl group in the TRP may allow the side chain of amino acid residue 5 of the TRP (arginine) to come into closer proximity with a key carboxyl residue on the receptor. A P5 citrulline analogue (i.e. SFLL Cit,(SEQ ID NO: 32) has demonstrated activity in platelets, and our LM and RA assays, and Nleu-P6 has demonstrated contractile activity in the GLM assay, suggesting that positive charge per se may not be the sole determinant governing the interaction of the residue at position 5 with the receptor. The stereochemical requirements for such an interaction are highlighted by the lack of agonist or antagonist activity of D-Arg-P5 in both the LM and RA assays. Yet the peptide SfLLr was an antagonist in the LM assay. In this regard, for the peptide-receptor interaction, the conserved aspartic and glutamic acid residues found in the sequences of many G-protein-linked receptors may be of particular significance.

N-acetylation abolished the biological activity of P5 and other TRPs. Thus, we speculate, without being bound to any theory, that a charge-charge interaction between the primary amino group and receptor carboxyl group may also be involved in the binding of the ligand to the receptor. Pr-P4 results in a receptor activation process that is distinct from the one triggered by P5 since: (1) Pr-P4 caused desensitization in the LM assay, whereas P5 and P5—NH$_2$ did not and (2) C-terminal amidation markedly enhanced the potency of P5 but abolished the activity of Pr-P4.

We tested the responses of the GLM and RA preparations to TRPs.

The responses of the GLM and RA preparations to all of the human receptor sequences tested, except for Pr-P4, are typified by the data for P5—NH$_2$ shown in FIG. 1; concentration-effect curves for the GLM and RA are shown in FIG. 2. As anticipated from previous results with N-acetylated TRPs, N-acetyl-P5 ($\leq$200 µM) was not active in either the GLM or RA assay, either as an agonist or as an antagonist of P5 (FIG. 2 and data not shown). Simply removing the P5 N-terminal hydroxyl group of serine (to form AP5), yielded a peptide with activity comparable to P5 (FIG. 2) This result was in keeping with our previous observations with a nonapeptide TRP beginning with alanine in position 42. Our next step involved deletion of the N-terminal amino group of AP5, to yield Pr-P4. Since we had already established that the tetrapeptide, $F_{43}LLR_{46}$, (P4, SEQ ID NO: 4) was inactive in the LM assay, it was unexpected that propionyl-P4, exhibited a thrombin-mimetic action in both the LM and RA bioassays (FIGS. 1 and 2). However, the responsiveness of the two tissues to Pr-P4 differed somewhat in comparison with the responses to P5 and P5NH$_2$: first, the GLM assay exhibited desensitization in response to the repeated administration of Pr-P4 (tracing B, FIG. 1), but not to P5—NH$_2$ or P5. Therefore, to measure a concentration-effect curve for Pr-P4, tissues yielding a standard response to 95 μM (60 μg/mL) P5 were exposed only to a single concentration of Pr-P4. The concentration-effect curve suggested partial agonist activity for Pr-P4 in the GLM tissue. When a tissue was desensitized by repeated exposure to Pr-P4, a diminished but measurable response towards P5 could still be monitored (tracing B, FIG. 1). A second qualitative difference between the action of Pr-P4 and P5 was observed in the RA assay system (FIG. 1), wherein Pr-P4 caused a persistent relaxation of the tissue, as opposed to the transient relaxation caused by P5, P5—NH$_2$ and the other TRPs tested. In the RA assay, Pr-P4 did not cause desensitization (not shown), and appeared to act as a full agonist (FIG. 2).

In contrast with acetylation of the amino-terminus of P5 (a substitution that abolished biological activity), esterification or amidation of the carboxyterminus of P5 resulted in an active peptide that was even more potent than the one having a free carboxyl group (FIGS. 1 and 2). Conversely, amidation of the carboxyterminus of Pr-P4 (to yield Pr-P4—NH$_2$) attenuated the activity of the peptide (FIG. 2) As a further control, we also ascertained that P3-amide was inactive (not shown), so as to indicate that amidation per se did not result in an active peptide. In view of the importance of the C-terminal arginine for the activity of P5, we tested the activity of the peptide wherein the L-arginine at position 46 was replaced with D-Arg. No response was observed to this analogue at concentrations as high as 400 μM in either the LM or RA assay, and the analogue did not exhibit antagonist activity. However, SfLLr was a weak antagonist. The pentapeptide, wherein the C-terminal arginine residue was replaced with lysine (PK5), was active in both the LM and RA assays, but exhibited a lower potency than that of P5 (FIG. 2). Nonetheless, a P5 derivative wherein R was replaced with Cit was active in the RA and LM assays. However, replacing the arginine with norleucine, to yield a peptide without a basic side-chain: $S_{42}$FLLNorleuN (SEQ ID NO: 33) or Nleu-P6 resulted in an agonist with an activity comparable to that of P5 in the GLM assay, but without activity in the RA assay at concentrations up to 120 μM (not shown).

The heptapeptide, $S_{42}FLLRNP_{48}$ (P7, SEQ ID NO: 34), representing the human receptor motif, is a sequence that is highly conserved amongst the thrombin receptors that have been cloned to date. The hamster and rat equivalent of P7, SFFLRNP (SEQ ID NO: 35), has a phenylalanine for leucine substitution at a position (no. 3) that has been observed to allow an alanine substitution without appreciably affecting peptide activity. In all of the receptors cloned to date, there is appreciable sequence variation beyond the proline residue. We compared the biological activity of the C-terminally extended version of P5 with P5 itself and evaluated the consequence of C-terminal amidation of P7 for comparison with the results obtained with P5-amide. As indicated in FIG. 2, P7 and P7—NH$_2$ were both active in the GLM and RA assay systems; and P7—NH$_2$ was more potent than either P5 or P7 in the two assays. A portion of this conserved sequence (F-P5, or $F_{43}LLRN_{47}$(SEQ ID NO: 36), reported previously to be an antagonist in platelets was inactive either as an agonist or antagonist in the GLM and RA assays at concentrations up to 200 μM.

We obtained an evaluation of the potencies of the various TRPs, relative to P5, by using the linear portions of the concentration-effect curves, so as to calculate for several response levels the average ratio of concentrations ($R_{EC}$) of an individual TRP, relative to concentration of P5 that caused the same contractile response (i.e. $R_{EC}$= $EC_{TRP}$÷$EC_{P5}$). Using this approach to calculate the relative effective concentration values ($R_{EC}$S, Table 2), the relative order of potencies of the agonists in the GLM assay (FIG. 2, upper, left to right) was: P7—NH$_2$≧P5-OCH3≈P5—NH$_2$>P7>Pr-P4 (partial agonist) ≈P5>AP5>PK5. In the RA assay, a similar approach to the estimate of relative potencies ($R_{EC}$S) was used, even though all agonists, except for P5—OCH$_3$, appeared to cause equivalent maximal relaxation (FIG. 2, lower). In the RA assay, the relative order of potencies (left to right, FIG. 2 lower) was: P7—NH$_2$≧P5-NH$_2$≈Pr-P4≧P5-OCH$_3$ (partial agonist) >P5≧P7>PK5≧AP5. Numerically, the relative potencies, as expressed by the $R_{EC}$ values relative to P5, are summarized in Table 2.

We compared the activities of the rat P5 sequences (i.e. Ra-P5 and Ra-P5—NH$_2$) as well as the activity of the rat P7 sequence (Ra-P7, SFFLRNP, SEQ ID NO: 35) with the activities of the human P5 and P7 sequences in the rat LM and RA bioassay systems. In keeping with previous structure-activity data for P5, in which a substitution at position 3 (i.e. SFALR, SEQ ID NO: 37) had little impact on the activity of the pentapeptide in a platelet assay our data revealed equivalent activities for rat P5 relative to human P5 and for rat P7, relative to the human P7 peptide, in the RLM assay (FIG. 3 upper). As with the human receptor P5 sequence, C-terminal amidation also increased the activity of the rat P5 peptide in the RLM assay, but with an even more dramatic effect on potency than was observed for the human P5 peptide (FIG. 3). Indeed, Ra-P5—NH$_2$ was the most potent of all of the peptides we examined in the RLM assay. In contrast with the activities of the rat receptor sequence peptides in the RLM assay, Ra-P5 and Ra-P5—NH$_2$ were considerably less potent than the comparable human receptor sequences in the RA assay. Significantly, Ra-P5 was four-fold less potent than P5 in the RA assay (FIG. 3, lower and Table 2), whereas P5 and Ra-P5 were equipotent in the RLM assay (FIG. 3, upper).

As illustrated in FIG. 4 (lanes C and D), the organ bath solution withdrawn from either a RLM or RA assay (30–60 μg/mL P5 or 47.5 to 95 μM), just after the peak of tissue response, was subjected to analysis by HPLC and compared with a standard solution of P5 made immediately before HPLC analysis either in buffer alone or in buffer that had been exposed to tissue under the conditions of a bioassay. The HPLC analysis (FIG. 4) demonstrated essentially quantitative recovery of the peptide from the RLM organ bath, without appreciable degradation (compare lane B, 1.2 μg from a P5 stock solution, with lane C, wherein a calculated amount of 1.1 μg P5 was expected from the organ bath solution). Quantitative recovery of P5 without appreciable degradation was also observed from the RA assay organ bath (lane D, FIG. 4). Similarly, P5—NH$_2$ was recovered essentially intact from both the RLM and RA organ baths (lanes E and F, FIG. 4). In FIG. 4, the peptide degradation products would have been eluted at retention times earlier than those of either P5 (17.33 min) or P5—NH$_2$ (16.83 min). Thus, during the relatively short time course of the tissue response (5–10 min), peptide proteolysis did not appear to be a factor that might affect the estimates of peptide potencies.

In our previous study, we established that in the GLM preparation, P5, like epidermal growth factor-urogastrone (EGF-URO), acts via the production of prostanoid metabolites, so as to be blocked by indomethacin. Like EGF-URO, but unlike bradykinin, the action of P5 in the GLM preparation was also selectively blocked by relatively low concentrations of the tyrosine kinase inhibitors, genistein (GS) and tyrphostin (TP)(14). We wished to determine if the active P5 analogues modified at the C-and N-terminus (represented by P5—NH$_2$ and Pr-P4) would also act in the GLM assay via the prostanoid-linked, tyrosine kinase-associated signal transduction pathway. We also wished to determine for the RA assay, wherein relaxation is caused by TRPs via the production of nitric oxide (5), whether the response might be sensitive to indomethacin and to the tyrosine kinase inhibitors, as is the case in the GLM assay. As illustrated for the GLM assay in FIG. 5 (right, tracings E, F, G and H), the contractile actions of both P5—NH$_2$ and Pr-P4 were blocked by either indomethacin or tyrphostin; genistein was similarly effective (not shown). Because of the desensitization caused by Pr-P4, in the experiments shown for the GLM in tracings G and H of FIG. 5, the initial tissue sensitivity to TRPs was evaluated by exposure to P5—NH$_2$ (5 μg/mL; 7.8 μM) before determining the effects of tyrphostin, genistein and indomethacin on Pr-P4 action (G, H, FIG. 5). In contrast, the responses of the RA, which were abolished with the nitric oxide synthase inhibitor, L-NAME (not shown), were not inhibited either by the tyrosine kinase inhibitors (FIG. 5, tracings A and C and data not shown) or by indomethacin (tracings B and D, FIG. 5). As illustrated by the representative experiments shown in FIG. 6, the response of the RLM preparation to P5-NH$_2$ was also quite sensitive to tyrphostin (not shown) and genistein (77±3% inhibition: mean ±S.E.M for n=6) but was only partially affected by indomethacin (40±6% inhibition: mean ±S.E.M. for n=6). In contrast, the contractile action of carbachol was unaffected in the RLM by either GS or Indo (FIG. 6). Thus, the actions of the TRPs in the gastric and aortic assays were differentially sensitive to indomethacin and the tyrosine kinase inhibitors.

Useful modifications to the N-terminal amino acids of the peptides or multimers of the present invention include the addition of acyl groups of from 1 to 3 carbon atoms. These additions would block the action of amino peptidase, thus increasing the biological half-life of these compounds.

Useful modifications to the C-terminal amino acids of the peptides or multimers of the present invention include the use of D-form amino acids, as well as addition of —B(OH)$_2$. These serve as carboxypeptidase blocking agents which also decrease metabolism of these compounds.

The peptides and compounds of the present invention are suitable for in vivo administration. They are soluble, including multimers using hydrophilic spacer arms. Their small size makes them less likely to be antigenic. Cyclization and modifications to the N- and C-terminal amino acids may be used to increase their resistance to metabolism. This increased metabolic resistance makes them suitable for oral administration. The formulation of suitable compositions for oral administration is well known to those skilled in the art.

They may also be administered parenterally, such as using intravenous or intramuscular administration. The formulation of suitable compositions for parenteral administration is well known to those skilled in the art.

The use of the peptides or compounds of the present invention for direct application to sites of tissue damage for wound healing is also anticipated. For such use they may be formulated in ointments, emulsions, and the like or they may be immobilized or derivatized on solid supports for prolonged exposure and dosing.

EXAMPLES

The following bioassay procedures were used in the Examples set forth below, unless otherwise noted.

The guinea pig gastric longitudinal muscle (GLM) strips and the rat thoracic aorta (RA) ring preparations were isolated as previously described 14, 15. In brief, gastric LM strips (3×10 mm), obtained from male albino Hartley strain guinea pigs were equilibrated for about 1.5 h at 37° (in an aerated (95% $O_2$/5% $CO_2$) Krebs-Henseleit buffer (3 mL) of the following composition (in mM): NaCl, 118; KCl, 4.7; $CaCl_2$, 2.5; $MgCl_2$, 1.2; $NaHCO_3$, 25; $KH_2PO_4$, 1.2; and glucose, 10. The pH was maintained at 7.4. Rat gastric LM strips (3×10 mm) were obtained, as for the GLM strips, from male albino Sprague Dawley animals (250–300 g). The stomach, opened along the greater curvature, was stripped free of all mucosal tissue under microscopic visualization and longitudinal tissue strips were cut exactly at right angles to the visible circular muscle bundles. Tissue strips were pre-equilibrated in the buffer described above. Each tissue was challenged twice each in succession at timed intervals with 50 nM carbachol (20 min intervals), 1 μM angiotensin-II (1 h intervals) and 95 μM (60 μg/mL) receptor pentapeptide (P5, SFLLR, SEQ ID NO: 2) (25 min intervals for GLM; 30–35 min for RLM; tissues were washed at 10 and 15 min after the additions of agonists. Contractions were monitored isometrically using Statham force-displacement transducers. Only tissues responding well to all three agonists were used further for the evaluation of the biological activities of P5 and other peptide agonists. For the GLM and RLM assays, concentration-effect curves for all peptides were constructed by expressing the response of each agonist as a percentage (% $P5_{95}$) relative to the contraction caused by 95 μM (60 μg/mL) P5 (0.9±0.1 g tension: mean ±S.E.M. for n=12 in the GLM; 1.6±0.9 g tension: mean ±S.E.M. for n=36 in the RLM).

Thoracic RA rings (2 mm×3 mm), obtained from male albino Sprague Dawley rats, were equilibrated (about 1 h, 37° ) in the same organ bath buffer as was used for the LM tissue, and tension (baseline 1.0 g) was monitored isometrically using either Statham or Grass force-displacement transducers. The presence of an intact endothelium was ascertained by monitoring a relaxation response to acetylcholine (ACh, 1 μM) in a preparation that was submaximally ($EC_{75}$) contracted by 0.1 μM noradrenaline (NA) in the presence of 0.1 mM ascorbic acid (to preserve the catecholamine). Only tissues yielding a relaxation concentration-response curve between 0.01 and 10 μM acetylcholine (maximal relaxation of 70 to 90%, relative to the tension developed by 0.1 μM NA) were used for the further evaluation of the receptor-derived peptides. The assay of TRP responsiveness was done (e.g. see FIG. 1) on tissues that were precontacted with 0.1 μM NA at 30 min time intervals. Tissues were washed approx. 5 min after the application of TRPs. In preliminary work studying the concentration-effect curve for P5 (see below), it was observed that 215 μM (137

μg/mL) of P5 yielded a nadir of relaxation in the RA preparation (on average, 62% relaxation of the NA-induced contractile response). Therefore, to construct concentration-effect curves and to normalize data between individual preparations, the relaxation responses to P5 and to the other TRPs were expressed as a percentage of the relaxation caused by 215 μM (137 μg/mL) of P5 (% $P5_{215}$). For purposes of comparison, the same stock solutions of an individual peptide were evaluated, relative to P5, in both the RA and LM bioassays. When possible, both assays were done simultaneously on the same day.

Weighed peptide samples were routinely dissolved in 50 mM phosphate buffer, pH 7.4, to yield stock solutions, from which volumes of up to 0.2 mL were added directly to the organ bath; the concentrations of all stock solutions used were verified by quantitative amino acid analysis of aliquots. Pr-P4 and Pr-P4—$NH_2$ were dissolved in 40 mM phosphate buffer, pH 7.4, containing 20% v/v absolute ethanol (i.e. 8 Vol of the above 50 mM phosphate buffer +2 Vol. ethanol). Control aliquots of the ethanol-containing phosphate buffer alone had no effect on either of the bioassay systems. Acetylcholine, carbachol, indomethacin, noradrenaline and angiotensin-II and thrombin (human, 3000 to 4000 U/mg; 1 U/mL≃10 nM) were from Sigma (St. Louis, Mo.); genistein (GS) was from ICN Biochemicals, Costa Mesa, Calif. Tyrphostin (TP) (RG 50864, also designated AG213) was obtained through the courtesy of Dr. R. R. Swillo, Rhone-Poulenc Rorer (Collegeville, Pa). Genistein and tyrphostin were dissolved in dimethylsulfoxide (DMSO) to yield a stock solution that, when diluted, resulted in a concentration of DMSO in the organ bath (<0.01% v/v) that alone had no effect on the bioassay systems. Indomethacin was dissolved in ethanol, such that the final ethanol concentration in the organ bath was at or lower than 0.01% v/v; this concentration of ethanol alone had no effect on the bioassay systems.

Example 1

Preparation of Linear Peptides

The thrombin receptor-derived polypeptides (based on the human receptor sequence), $S_{42}FL_{44}$-amide(P3-$NH_2$), N-propionyl-$F_{43}LLR_{46}$ (Pr-P4, SEQ ID NO:38), N-propionyl-$F_{43}$-$LLR_{46}$-amide(Pr-P4-$NH_2$, SEQ ID NO:39), $S_{42}FLLR_{46}$(P5, SEQ ID NO: 2 ), $S_{42}FLLK_{46}$(PK5, SEQ ID NO: 40), $S_{42}FLL$-$r_{46}$(D-Arg-P5 ), $A_{42}FLLR_{46}$(AP5, SEQ ID NO:41), N-acetyl-$S_{42}FLLR_{46}$(N-Ac-P5, SEQ ID NO:42), $S_{42}FLLR_{46}$—amide(P5—$NH_2$, SEQ ID NO:43), $S_{42}FLLR_{46}$-O-Methyl (P5-$OCH_3$, SEQ ID NO:44), $F_{43}$-$LLRN_{47}$ (F-P5, SEQ ID NO:45), $S_{42}FLLNorleuN_{47}$ (Nleu-P6, SEQ ID NO:33), $S_{42}FLLRNP_{48}$ (P7, SEQ ID NO:34) and $S_{42}FLLRNP_{48}$-amide (P7—$NH_2$, SEQ ID NO:45) were prepared by standard solid phase synthesis procedures either in our own laboratory 18 (t-Boc procedures for P7, Nleu-P6, P5-$OCH_3$ and P3—$NH_2$) or in the Core Peptide Synthesis Laboratory at the Department of Biochemistry, Queens University, Kingston, Ontario, Canada (Fmoc procedures for Pr-P4, Pr-P4—$NH_2$P5, AP5, P5—$NH_2$, F-P5 and P7—$NH_2$). The rat receptor sequence TRPs, SFFLR (Ra-P5, SEQ ID NO:46) and SFFLR-amide (Ra-P5—$NH_2$, SEQ ID NO:47) were also from the Queens University laboratory; the heptapeptide based on the rat receptor sequence, SFFL-RNP (Ra-P7, SEQ ID NO:35), was prepared in our own laboratory as for P7 using a t-Boc procedure. Pr-P4 was prepared using propionic acid/DCC to react with resin-bound P4 prior to deprotection; P5-Methyl ester was prepared by treating the resin-attached peptide with 50 milliequivalents of triethylamine in 20 mL methanol. The peptide ester so released from the resin was deprotected with anhydrous HF. Peptides released from the resin and deprotected were then purified to homogeneity (single peak by analytical reversed phase high performance liquid chromatography: Vydac RPC18 column, acetonitrile gradient in 0.1% trifluoroacetic acid). Peptide compositions were confirmed by amino acid analysis and, where appropriate (Pr-P4, Pr-P4-amide), by mass spectral analysis.

Example 2

Preparation of a Cyclic Tetrapeptide

2-Orthochloro trityl resin (1g, 1.4–1.6 meq Cl/g resin) in dry dichloromethane (10 mL) was stirred in a round bottom flask. Diisopropylethylamine (DIPEA) (0.765 mL, 4.5 mmol) and Na-Fmoc-Leu-OH (530 mg, 1.5 mmol) were added and the solution was stirred for 45 min at room temperature. A mixture of MeOH (0.12 ml, 3 mmol) and DIPEA (1.02 mL, 6 mmol) was then added and the mixture stirred for another 10 min at room temperature. The Fmoc-Leu-resin was filtered and subsequently washed with DMF (3×20 mL) i-PrOH (3×10 ml.), Et20 (2×10 mL) and dried in vacuo for 24 h at room temperature. The loading of the amino acid per gram of substituted resin was 0.5 mmol/g calculated by weight and amino acid analysis.

Na-Fmoc-Leu-2-orthochloro trityl chloride resin (557 mg, 0.5 mmol/g), was used for the synthesis of the H-Leu-Arg(PMC)-Phe-Leu-OH linear peptide precursor following the protocol shown in Table 1. The finished peptide-resin (after Fmoc-deprotection of the last amino acid, shown in Step 4) was dried in vacuo (650 mg) and was treated with the splitting mixture DCM/AcOH/TFE (6.5 mL, 7:1:2) for 1 h at room temperature to remove the peptide from the resin. The mixture was filtered off and the resin washed several times with the splitting mixture and DCM. The solvent was removed on a rotary evaporator and the oily product obtained was precipitated from dry diethylether as a white solid (82 mg) salt of the linear peptide precursor (II). The white powder was stored in the refrigerator for 18 h.

To a solution of the linear tetrapeptide precursor salt (II) (82 mg, 0.1 mmol) in DMF (23 ml) containing DIPEA (1.5% v/v, 0.35 ml), BOP reagent (265.2 mg, 0.5 mmol) was added. The reaction mixture was stirred for 98 h at room temperature and the solvent was removed under reduced pressure, yielding a light yellow oily residue (III). The reaction was followed by the ninhydrin test on TLC using $CHCl_3$/MeoH (6:1) as the solvent system.

The oily residue (III) was treated with 60% TFA in DCM (1.5 mL) containing 1% Anisole as scavenger for 2 h at room temperature. The resulting solution was concentrated to a small volume (0.5 mL). A few drops of MeOH were added and then the final free cyclic tetrapeptide was precipitated as a white amorphous solid upon addition of diethylether (45 mg). The Rf on TLC using NBuOH-AcOH-H20 (4:1:1) was 0.67.

Example 3

Activity of Linear TRPs

The relative potencies of linear TRPs in the LM and RA assays were evaluated using the bioassays previously described.

Results are shown in Table 2.

TABLE 2

Relative potencies of TRPs in the LM and RA assays.

|  |  | GLM | RLM | RA |
|---|---|---|---|---|
| Propionyl $F_{43}LLR_{46}$ (SEQ ID NO: 38) | Pr-P4 | $1^b$ |  | 0.1 |
| Propionyl $F_{43}LLR_{46}$-$NH_2$ (SEQ ID NO: 39) | Pr-P4-$NH_2$ | N.A.$^c$ |  | A.$^c$ |
| $S_{42}FLLR_{46}$ (SEQ ID NO: 2) | P5 | 1 | 1 | 1 |
| $S_{42}FFLR_{46}$ (SEQ ID NO: 46) | Ra-P5 |  | 1.0 | 4.4 |
| $S_{42}FFLK_{46}$ (SEQ ID NO: 40) | PK5 | 4.5 |  | 1.3 |
| $S_{42}FLLr_{46}$ | D-Arg-P5 | N.A.$^c$ |  | N.A.$^c$ |
| $A_{42}FLLR_{46}$ (SEQ ID NO: 41) | AP5 | 1.8 |  | 1.7 |
| $F_{43}LLRN_{47}$ (SEQ ID NO: 36) | F-P5 | N.A.$^c$ |  | N.A.$^c$ |
| Acetyl-$S_{42}FLLR_{46}$ (SEQ ID NO: 42) | Ac-P5 | N.A.$^c$ |  | N.A.$^c$ |
| $S_{42}FLLR_{46}$-$NH_2$ (SEQ ID NO: 43) | P5-$NH_2$ | 0.1 | 0.2 | 0.1 |
| $S_{42}FFLR_{46}$-$NH_2$ (SEQ ID NO: 47) | Ra-P5-$NH_2$ |  | 0.07 | 0.2 |
| $S_{42}FLLR_{46}$-$OCH_3$ (SEQ ID NO: 44) | P5-$OCH_3$ | 0.1 |  | $0.1^b$ |
| $S_{42}FLLNleuN_{47}$ (SEQ ID NO: 33) | Nleu-P6 | A.$^c$ |  | N.A.$^c$ |
| $S_{42}FLLRNP_{48}$ (SEQ ID NO: 34) | P7 | 0.4 | 0.3 | 1.1 |
| $S_{42}FFLRNP_{48}$ (SEQ ID NO: 35) | Ra-P7 |  | 0.3 | 0.6 |
| $S_{42}FLLRNP_{48}$-$NH_2$ (SEQ ID NO: 45) | P7-$NH_2$ | 0.04 | 0.1 | 0.08 |

$^a$. The relative potencies for all agonists were determined by using several points on the linear portions of the concentration-effect curves shown in FIGS. 2 and 3 to estimate for each agonist an average concentration ratio ($R_{EC}$), relative to a concentration of P5 that caused an equal response, as outlined in the text. The numbering of amino acid residues is based on the human receptor sequence.
$^b$. partial agonist properties.
$^c$. N.A. = not active; A. active, but no able to determine $R_{EC}$.

Example 4

Activity of Cyclic TRPs

Cyclic TRPs were evaluated using the bioassays previously described.

Results are shown in Table 3.

TABLE 3

Activity of cyclic TRP.

| Compound | Concentration Tested μM | Activity relative to SFLLR (SEQ ID NO:2) (P-5) ($EC_{cyclic}/EC_{P-5}$) |
|---|---|---|
| ⌐SFLLR⌐<br>└─────┘<br>(SEQ ID NO:2) | 9 μM | not active at this concentration; higher concentrations not yet tested |
| ⌐SFLLR⌐<br>└─Aca─┘<br>(SEQ ID NO:9) | 30 to 60 μM | 1 |
| ⌐FLLR⌐<br>└────┘<br>(SEQ ID NO:4) | 30 to 90 μm | 2 |
| ⌐FLLR⌐<br>└─Aca─┘<br>(SEQ ID NO:8) | 30 to 125 μM | 2 |
| ⌐FLLR⌐<br>└─G─┘<br>(SEQ ID NO:48) | 200 μM | 4 |

It will be apparent to one of ordinary skill in the art that various changes and modifications of an obvious nature may be made without departing from the spirit of the invention, and all such modifications are considered to fall within the scope of the invention, as defined by the appended claims.

What is claimed is:

1. A cyclic peptide based on the N-terminal domain of the human G-protein linked thrombin receptor sequence.

2. The cyclic peptide of claim 1 comprising the amino acid sequence:

$$\boxed{X_1 \Psi X_2 X_3 \Omega X_4}$$

wherein $\psi$ is selected from the group consisting of natural aromatic amino acids and non-natural aromatic amino acids; $\Omega$ is selected from the group consisting of natural basic amino acids, non-natural basic amino acids and derivatives of said natural and non-natural basic amino acids; $X_1$ is selected from the group consisting of no amino acid, natural amino acids, derivatives of said natural amino acids, acyls of from 1 to about 3 carbon atoms and alkyls of from 1 to about 5 carbon atoms; $X_2$ is any natural amino acid; $X_3$ is selected from the group consisting of no amino acid and any natural amino acid; and $X_4$ is selected from the group consisting of no amino acid, natural amino acids, and derivatives of said natural amino acids.

3. The cyclic peptide of claim 1 comprising the amino acid sequence:

$$\boxed{X_1\Psi X_2 X_3 \Omega X_4}$$

wherein $\psi$ is any natural aromatic amino acid; $\Omega$ is any natural basic amino acid; $X_1$ is selected from the group consisting of no amino acid and natural amino acids; $X_2$ and $X_3$ are, independently, any natural amino acid; and $X_4$ is selected from the group consisting of no amino acid, natural amino acids, and non-natural amino acids.

4. A cyclic peptide based on the N-terminal domain of the human G-protein linked thrombin receptor sequence selected from the group consisting of:

$$\boxed{\text{SFLLRAca}},$$

$$\boxed{\text{FLLR}},$$

$$\boxed{\text{FLLRAca}}, \text{ and}$$

$$\boxed{\text{FLLRG}}.$$

5. A cyclic peptide based on the N-terminal domain of the human G-protein linked thrombin receptor sequence which is:

$$\boxed{\text{FLLRK}}.$$

6. The cyclic peptide of claim 1 which is:

$$\boxed{\text{FLLRX}},$$

wherein X is a hydrophobic amino acid.

* * * * *

SEQUENCE LISTING ( 1 ) GENERAL INFORMATION:

( i i i ) NUMBER OF SEQUENCES: 50

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Ser  Phe  Leu  Leu  Arg  Asn  Pro  Asn  Asp  Lys  Tyr  Glu  Pro  Phe
    1                  5                              10

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( D ) TOPOLOGY: both ( i i ) MOLECULE TYPE: peptide ( x i ) SEQUENCE DESCRIPTION: SEQ ID NO:2:

Ser Phe Leu Leu Arg
1               5

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Xaa1
            / note="Xaa1 may be no AA, a nat/non-nat AA or
            derivative, an acyl, an alkyl, an aryl, or an
            alkylaryl."

( i x ) FEATURE:
        ( A ) NAME/KEY: Modified-site
        ( B ) LOCATION: 2
        ( D ) OTHER INFORMATION: /label=Xaa2
            / note="Xaa2 is a nat/non-nat aromatic AA or
            derivative."

( i x ) FEATURE:
        ( A ) NAME/KEY: Modified-site
        ( B ) LOCATION: 3
        ( D ) OTHER INFORMATION: /label=Xaa3
            / note="Xaa3 may be no AA, a nat/non-nat AA or
            derivative"

( i x ) FEATURE:
        ( A ) NAME/KEY: Modified-site
        ( B ) LOCATION: 4
        ( D ) OTHER INFORMATION: /label=Xaa4
            / note="Xaa4 may be no AA, a nat/non-nat AA or
            derivative"

( i x ) FEATURE:
        ( A ) NAME/KEY: Modified-site
        ( B ) LOCATION: 5
        ( D ) OTHER INFORMATION: /label=Xaa5
            / note="Xaa5 is a nat/non-nat basic AA or
            derivative"

( i x ) FEATURE:
        ( A ) NAME/KEY: Modified-site
        ( B ) LOCATION: 6
        ( D ) OTHER INFORMATION: /label=Xaa6
            / note="Xaa6 may be B(OH)2, no AA or a
            nat/non-nat AA or derivative"

( x i ) SEQUENCE DESCRIPTION: SEQ ID NO:3:

Xaa Xaa Xaa Xaa Xaa Xaa
1               5

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( D ) TOPOLOGY: both ( i i ) MOLECULE TYPE: peptide ( x i ) SEQUENCE DESCRIPTION: SEQ ID NO:4:

Phe Leu Leu Arg
1

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 5
        ( D ) OTHER INFORMATION: /label=Arg
            / note="Arg is acetylated"

( x i ) SEQUENCE DESCRIPTION: SEQ ID NO:5:

Ser Phe Leu Leu Arg
1                   5

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 4
        ( D ) OTHER INFORMATION: /label=Arg
            / note="Arg is acetylated"

( x i ) SEQUENCE DESCRIPTION: SEQ ID NO:6:

Phe Leu Leu Arg
1

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 3
        ( D ) OTHER INFORMATION: /label=Xaa
            / note="Xaa is no AA, Gly, Acp or Lys"

( x i ) SEQUENCE DESCRIPTION: SEQ ID NO:7:

Leu Arg Xaa Ser Phe Leu
1                   5

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( D ) TOPOLOGY: circular ( i i ) MOLECULE TYPE: peptide ( i x ) FEATURE:
  ( A ) NAME/KEY: Modified-site
  ( B ) LOCATION: 5
  ( D ) OTHER INFORMATION: /label=Xaa
    / note="Xaa is Acp."

( x i ) SEQUENCE DESCRIPTION: SEQ ID NO:8:

Phe Leu Leu Arg Xaa
1             5

( 2 ) INFORMATION FOR SEQ ID NO:9:

( i ) SEQUENCE CHARACTERISTICS:
    ( A ) LENGTH: 6 amino acids
    ( B ) TYPE: amino acid
    ( D ) TOPOLOGY: circular ( i i ) MOLECULE TYPE: peptide ( i x ) FEATURE:
    ( A ) NAME/KEY: Modified-site
    ( B ) LOCATION: 6
    ( D ) OTHER INFORMATION: /label=Xaa
      / note="Xaa is Acp."

( x i ) SEQUENCE DESCRIPTION: SEQ ID NO:9:

Ser Phe Leu Leu Arg Xaa
1             5

( 2 ) INFORMATION FOR SEQ ID NO:10:

( i ) SEQUENCE CHARACTERISTICS:
    ( A ) LENGTH: 4 amino acids
    ( B ) TYPE: amino acid
    ( D ) TOPOLOGY: circular ( i i ) MOLECULE TYPE: peptide ( x i ) SEQUENCE DESCRIPTION: SEQ ID NO:10:

Arg Leu Leu Phe
1

( 2 ) INFORMATION FOR SEQ ID NO:11:

( i ) SEQUENCE CHARACTERISTICS:
    ( A ) LENGTH: 5 amino acids
    ( B ) TYPE: amino acid
    ( D ) TOPOLOGY: circular ( i i ) MOLECULE TYPE: peptide ( x i ) SEQUENCE DESCRIPTION: SEQ ID NO:11:

Ser Arg Leu Leu Phe
1             5

( 2 ) INFORMATION FOR SEQ ID NO:12:

( i ) SEQUENCE CHARACTERISTICS:
    ( A ) LENGTH: 5 amino acids
    ( B ) TYPE: amino acid
    ( D ) TOPOLOGY: circular ( i i ) MOLECULE TYPE: peptide ( i x ) FEATURE:
    ( A ) NAME/KEY: Modified-site
    ( B ) LOCATION: 5
    ( D ) OTHER INFORMATION: /label=Xaa
      / note="Xaa is Acp."

( x i ) SEQUENCE DESCRIPTION: SEQ ID NO:12:

```
Arg  Leu  Leu  Phe  Xaa
1                   5
```

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 6
        ( D ) OTHER INFORMATION: /label=Xaa
            / note="Xaa is Acp."

( x i ) SEQUENCE DESCRIPTION: SEQ ID NO:13:

```
Ser  Arg  Leu  Leu  Phe  Xaa
1                        5
```

( 2 ) INFORMATION FOR SEQ ID NO:14:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

```
Ser  Phe  Leu  Leu
1
```

( 2 ) INFORMATION FOR SEQ ID NO:15:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Xaa1
            / note="Xaa1 may be any nat/non-nat D- or L-AA"

( i x ) FEATURE:
        ( A ) NAME/KEY: Modified-site
        ( B ) LOCATION: 2
        ( D ) OTHER INFORMATION: /label=Phe
            / note="Phe may be substituted w/ any
            nat/non-nat aromatic (position 2) AA or derivative
            w/ positive charge or H-bonding group at position 5."

( i x ) FEATURE:
        ( A ) NAME/KEY: Modified-site
        ( B ) LOCATION: 3
        ( D ) OTHER INFORMATION: /label=Xaa3
            / note="Xaa3 may be any nat/non-nat D- or L-AA"

( i x ) FEATURE:
        ( A ) NAME/KEY: Modified-site
        ( B ) LOCATION: 4
        ( D ) OTHER INFORMATION: /label=Xaa4
            / note="Xaa4 may be any nat/non-nat D- or L-AA"

( i x ) FEATURE:
        ( A ) NAME/KEY: Modified-site
        ( B ) LOCATION: 5
        ( D ) OTHER INFORMATION: /label=Arg
            / note="Arg may be substituted w/ any nat/non-nat aromatic (position 2) AA or derivative
w/ positive charge or H-bonding group at position 5"

( x i ) SEQUENCE DESCRIPTION: SEQ ID NO:15:

```
Xaa  Phe  Xaa  Xaa  Arg
1                    5
```

( 2 ) INFORMATION FOR SEQ ID NO:16:

( i ) SEQUENCE CHARACTERISTICS:
        ( A ) LENGTH: 6 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 1
        ( D ) OTHER INFORMATION: /label=Xaa1
            / note="Xaa1 may be no AA, any nat/non-nat AA or
            a hydrophilic spacer"

( i x ) FEATURE:
        ( A ) NAME/KEY: Modified-site
        ( B ) LOCATION: 3
        ( D ) OTHER INFORMATION: /label=Xaa3
            / note="Xaa3 may be Phe, fluoroPhe, Tyr, His,
            Cha or D- Phe"

( i x ) FEATURE:
        ( A ) NAME/KEY: Modified-site
        ( B ) LOCATION: 6
        ( D ) OTHER INFORMATION: /label=Xaa6
            / note="Xaa6 may be Arg, Lys, Orn or D-Arg"

( x i ) SEQUENCE DESCRIPTION: SEQ ID NO:16:

```
Xaa  Ser  Xaa  Leu  Leu  Xaa
1                    5
```

( 2 ) INFORMATION FOR SEQ ID NO:17:

( i ) SEQUENCE CHARACTERISTICS:
        ( A ) LENGTH: 5 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 1
        ( D ) OTHER INFORMATION: /label=Xaa1
            / note="Xaa1 may be no AA, any nat/non-nat AA or
            a hydrophilic spacer"

( i x ) FEATURE:
        ( A ) NAME/KEY: Modified-site
        ( B ) LOCATION: 2
        ( D ) OTHER INFORMATION: /label=Xaa2
            / note="Xaa2 may be Phe, fluoroPhe, Tyr, His,
            Cha or D- Phe"

( i x ) FEATURE:
        ( A ) NAME/KEY: Modified-site
        ( B ) LOCATION: 5
        ( D ) OTHER INFORMATION: /label=Xaa5
            / note="Xaa5 may be Arg, Lys, Orn or D-Arg"

( x i ) SEQUENCE DESCRIPTION: SEQ ID NO:17:

```
Xaa  Xaa  Leu  Leu  Xaa
1                    5
```

( 2 ) INFORMATION FOR SEQ ID NO:18:

( i ) SEQUENCE CHARACTERISTICS:
    ( A ) LENGTH: 6 amino acids
    ( B ) TYPE: amino acid
    ( D ) TOPOLOGY: circular ( i i ) MOLECULE TYPE: peptide ( i x ) FEATURE:
    ( A ) NAME/KEY: Modified-site
    ( B ) LOCATION: 1
    ( D ) OTHER INFORMATION: /label=Xaa1
        / note="Xaa1 may be no AA, any nat/non-nat AA or
        a hydrophilic spacer"

( i x ) FEATURE:
    ( A ) NAME/KEY: Modified-site
    ( B ) LOCATION: 3
    ( D ) OTHER INFORMATION: /label=Xaa3
        / note="Xaa3 may be Arg, Lys, Orn or D-Arg"

( i x ) FEATURE:
    ( A ) NAME/KEY: Modified-site
    ( B ) LOCATION: 6
    ( D ) OTHER INFORMATION: /label=Xaa6
        / note="Xaa6 may be Phe, fluoroPhe, Tyr, His,
        Cha or D- Phe"

( x i ) SEQUENCE DESCRIPTION: SEQ ID NO:18:

Xaa  Ser  Xaa  Leu  Leu  Xaa
1                            5

( 2 ) INFORMATION FOR SEQ ID NO:19:

( i ) SEQUENCE CHARACTERISTICS:
    ( A ) LENGTH: 5 amino acids
    ( B ) TYPE: amino acid
    ( D ) TOPOLOGY: circular ( i i ) MOLECULE TYPE: peptide ( i x ) FEATURE:
    ( A ) NAME/KEY: Modified-site
    ( B ) LOCATION: 1
    ( D ) OTHER INFORMATION: /label=Xaa1
        / note="Xaa1 may be no AA, any nat/non-nat AA or
        a hydrophilic spacer"

( i x ) FEATURE:
    ( A ) NAME/KEY: Modified-site
    ( B ) LOCATION: 2
    ( D ) OTHER INFORMATION: /label=Xaa2
        / note="Xaa2 may be Arg, Lys, Orn or D-Arg"

( i x ) FEATURE:
    ( A ) NAME/KEY: Modified-site
    ( B ) LOCATION: 5
    ( D ) OTHER INFORMATION: /label=Xaa5
        / note="Xaa5 may be Phe, fluoroPhe, Tyr, His,
        Cha or D- Phe"

( x i ) SEQUENCE DESCRIPTION: SEQ ID NO:19:

Xaa  Xaa  Leu  Leu  Xaa
1                        5

( 2 ) INFORMATION FOR SEQ ID NO:20:

( i ) SEQUENCE CHARACTERISTICS:
    ( A ) LENGTH: 5 amino acids
    ( B ) TYPE: amino acid
    ( D ) TOPOLOGY: circular ( i i ) MOLECULE TYPE: peptide ( i x ) FEATURE:
    ( A ) NAME/KEY: Modified-site ( B ) LOCATION: 1
( D ) OTHER INFORMATION: /label=Xaa1
/ note="Xaa1 may be no AA, any nat/non-nat AA or a hydrophilic spacer"

( i x ) FEATURE:
( A ) NAME/KEY: Modified-site
( B ) LOCATION: 4
( D ) OTHER INFORMATION: /label=Xaa4
/ note="Xaa4 may be Pro, Hypro, Azc, Pip or Sar"

( x i ) SEQUENCE DESCRIPTION: SEQ ID NO:20:

Xaa Ser Phe Xaa Arg
1               5

( 2 ) INFORMATION FOR SEQ ID NO:21:

( i ) SEQUENCE CHARACTERISTICS:
( A ) LENGTH: 4 amino acids
( B ) TYPE: amino acid
( D ) TOPOLOGY: circular ( i i ) MOLECULE TYPE: peptide ( i x ) FEATURE:
( A ) NAME/KEY: Modified-site
( B ) LOCATION: 1
( D ) OTHER INFORMATION: /label=Xaa1
/ note="Xaa1 may be no AA, any nat/non-nat AA or a hydrophilic spacer"

( i x ) FEATURE:
( A ) NAME/KEY: Modified-site
( B ) LOCATION: 3
( D ) OTHER INFORMATION: /label=Xaa3
/ note="Xaa3 may be Pro, HyPro, Azc, Pip or Sar"

( x i ) SEQUENCE DESCRIPTION: SEQ ID NO:21:

Xaa Phe Xaa Arg
1

( 2 ) INFORMATION FOR SEQ ID NO:22:

( i ) SEQUENCE CHARACTERISTICS:
( A ) LENGTH: 5 amino acids
( B ) TYPE: amino acid
( D ) TOPOLOGY: circular ( i i ) MOLECULE TYPE: peptide ( i x ) FEATURE:
( A ) NAME/KEY: Modified-site
( B ) LOCATION: 1
( D ) OTHER INFORMATION: /label=Xaa1
/ note="Xaa1 may be no AA, any nat/non-nat AA or a hydrophilic spacer"

( i x ) FEATURE:
( A ) NAME/KEY: Modified-site
( B ) LOCATION: 4
( D ) OTHER INFORMATION: /label=Xaa4
/ note="Xaa4 may be Pro, HyPro, Azc, Pip or Sar"

( x i ) SEQUENCE DESCRIPTION: SEQ ID NO:22:

Xaa Ser Arg Xaa Phe
1               5

( 2 ) INFORMATION FOR SEQ ID NO:23:

( i ) SEQUENCE CHARACTERISTICS:
( A ) LENGTH: 4 amino acids
( B ) TYPE: amino acid
( D ) TOPOLOGY: circular ( i i ) MOLECULE TYPE: peptide ( i x ) FEATURE:
        ( A ) NAME/KEY: Modified-site
        ( B ) LOCATION: 1
        ( D ) OTHER INFORMATION: /label=Xaa1
            / note="Xaa1 may be no AA, any nat/non-nat AA or
            a hydrophilic spacer"

( i x ) FEATURE:
        ( A ) NAME/KEY: Modified-site
        ( B ) LOCATION: 3
        ( D ) OTHER INFORMATION: /label=Xaa3
            / note="Xaa3 may be Pro, HyPro, Azc, Pip or Sar"

( x i ) SEQUENCE DESCRIPTION: SEQ ID NO:23:

Xaa Arg Xaa Phe
1

( 2 ) INFORMATION FOR SEQ ID NO:24:

( i ) SEQUENCE CHARACTERISTICS:
        ( A ) LENGTH: 5 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 3
        ( D ) OTHER INFORMATION: /label=Xaa3
            / note="Xaa3 may be Asp or Glu"

( i x ) FEATURE:
        ( A ) NAME/KEY: Modified-site
        ( B ) LOCATION: 4
        ( D ) OTHER INFORMATION: /label=Xaa4
            / note="Xaa4 may be Lys or Orn"

( x i ) SEQUENCE DESCRIPTION: SEQ ID NO:24:

Ser Phe Xaa Xaa Arg
1                  5

( 2 ) INFORMATION FOR SEQ ID NO:25:

( i ) SEQUENCE CHARACTERISTICS:
        ( A ) LENGTH: 5 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 3
        ( D ) OTHER INFORMATION: /label=Xaa3
            / note="Xaa3 may be Lys or Orn"

( i x ) FEATURE:
        ( A ) NAME/KEY: Modified-site
        ( B ) LOCATION: 4
        ( D ) OTHER INFORMATION: /label=Xaa4
            / note="Xaa4 may be Asp or Glu"

( x i ) SEQUENCE DESCRIPTION: SEQ ID NO:25:

Ser Phe Xaa Xaa Arg
1                  5

( 2 ) INFORMATION FOR SEQ ID NO:26:

( i ) SEQUENCE CHARACTERISTICS:
        ( A ) LENGTH: 4 amino acids
        ( B ) TYPE: amino acid ( D ) TOPOLOGY: circular ( i i ) MOLECULE TYPE: peptide ( i x ) FEATURE:
    ( A ) NAME/KEY: Modified-site
    ( B ) LOCATION: 2
    ( D ) OTHER INFORMATION: /label=Xaa2
        / note="Xaa2 may be Asp or Glu"

( i x ) FEATURE:
    ( A ) NAME/KEY: Modified-site
    ( B ) LOCATION: 3
    ( D ) OTHER INFORMATION: /label=Xaa3
        / note="Xaa3 may be Lys or Orn"

( x i ) SEQUENCE DESCRIPTION: SEQ ID NO:26:

Phe Xaa Xaa Arg
1

( 2 ) INFORMATION FOR SEQ ID NO:27:

( i ) SEQUENCE CHARACTERISTICS:
        ( A ) LENGTH: 4 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 2
        ( D ) OTHER INFORMATION: /label=Xaa2
            / note="Xaa2 may be Lys or Orn"

( i x ) FEATURE:
        ( A ) NAME/KEY: Modified-site
        ( B ) LOCATION: 3
        ( D ) OTHER INFORMATION: /label=Xaa3
            / note="Xaa3 may be Asp or Glu"

( x i ) SEQUENCE DESCRIPTION: SEQ ID NO:27:

Phe Xaa Xaa Arg
1

( 2 ) INFORMATION FOR SEQ ID NO:28:

( i ) SEQUENCE CHARACTERISTICS:
        ( A ) LENGTH: 5 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 3
        ( D ) OTHER INFORMATION: /label=Xaa3
            / note="Xaa3 may be Asp or Glu"

( i x ) FEATURE:
        ( A ) NAME/KEY: Modified-site
        ( B ) LOCATION: 4
        ( D ) OTHER INFORMATION: /label=Xaa4
            / note="Xaa4 may be Lys or Orn"

( x i ) SEQUENCE DESCRIPTION: SEQ ID NO:28:

Ser Arg Xaa Xaa Phe
1               5

( 2 ) INFORMATION FOR SEQ ID NO:29:

( i ) SEQUENCE CHARACTERISTICS:
        ( A ) LENGTH: 5 amino acids ( B ) TYPE: amino acid
            ( D ) TOPOLOGY: circular ( i i ) MOLECULE TYPE: peptide ( i x ) FEATURE:
            ( A ) NAME/KEY: Modified-site
            ( B ) LOCATION: 3
            ( D ) OTHER INFORMATION: /label=Xaa3
                    / note="Xaa3 may be Lys or Orn"

( i x ) FEATURE:
            ( A ) NAME/KEY: Modified-site
            ( B ) LOCATION: 4
            ( D ) OTHER INFORMATION: /label=Xaa4
                    / note="Xaa4 may be Asp or Glu"

( x i ) SEQUENCE DESCRIPTION: SEQ ID NO:29:

Ser  Arg  Xaa  Xaa  Phe
1                    5

( 2 ) INFORMATION FOR SEQ ID NO:30:

( i ) SEQUENCE CHARACTERISTICS:
            ( A ) LENGTH: 4 amino acids
            ( B ) TYPE: amino acid
            ( D ) TOPOLOGY: circular ( i i ) MOLECULE TYPE: peptide ( i x ) FEATURE:
            ( A ) NAME/KEY: Modified-site
            ( B ) LOCATION: 2
            ( D ) OTHER INFORMATION: /label=Xaa2
                    / note="Xaa2 may be Glu or Asp"

( i x ) FEATURE:
            ( A ) NAME/KEY: Modified-site
            ( B ) LOCATION: 3
            ( D ) OTHER INFORMATION: /label=Xaa3
                    / note="Xaa3 may be Lys or Orn"

( x i ) SEQUENCE DESCRIPTION: SEQ ID NO:30:

Arg  Xaa  Xaa  Phe
1

( 2 ) INFORMATION FOR SEQ ID NO:31:

( i ) SEQUENCE CHARACTERISTICS:
            ( A ) LENGTH: 4 amino acids
            ( B ) TYPE: amino acid
            ( D ) TOPOLOGY: circular ( i i ) MOLECULE TYPE: peptide ( i x ) FEATURE:
            ( A ) NAME/KEY: Modified-site
            ( B ) LOCATION: 2
            ( D ) OTHER INFORMATION: /label=Xaa2
                    / note="Xaa2 may be Lys or Orn"

( i x ) FEATURE:
            ( A ) NAME/KEY: Modified-site
            ( B ) LOCATION: 3
            ( D ) OTHER INFORMATION: /label=Xaa3
                    / note="Xaa3 may be Asp or Glu"

( x i ) SEQUENCE DESCRIPTION: SEQ ID NO:31:

Arg  Xaa  Xaa  Phe
1

( 2 ) INFORMATION FOR SEQ ID NO:32:

( i ) SEQUENCE CHARACTERISTICS:

(A) LENGTH: 5 amino acids
(B) TYPE: amino acid
(D) TOPOLOGY: linear (ii) MOLECULE TYPE: peptide (ix) FEATURE:
(A) NAME/KEY: Modified-site
(B) LOCATION: 5
(D) OTHER INFORMATION: /label=Xaa
/ note="Xaa is Cit"

(xi) SEQUENCE DESCRIPTION: SEQ ID NO:32:

Ser Phe Leu Leu Xaa
1               5

(2) INFORMATION FOR SEQ ID NO:33:

(i) SEQUENCE CHARACTERISTICS:
(A) LENGTH: 6 amino acids
(B) TYPE: amino acid
(D) TOPOLOGY: linear (ii) MOLECULE TYPE: peptide (ix) FEATURE:
(A) NAME/KEY: Modified-site
(B) LOCATION: 5
(D) OTHER INFORMATION: /label=Xaa
/ note="Xaa is Norleu"

(xi) SEQUENCE DESCRIPTION: SEQ ID NO:33:

Ser Phe Leu Leu Xaa Asn
1               5

(2) INFORMATION FOR SEQ ID NO:34:

(i) SEQUENCE CHARACTERISTICS:
(A) LENGTH: 7 amino acids
(B) TYPE: amino acid
(D) TOPOLOGY: linear (ii) MOLECULE TYPE: peptide (xi) SEQUENCE DESCRIPTION: SEQ ID NO:34:

Ser Phe Leu Leu Arg Asn Pro
1               5

(2) INFORMATION FOR SEQ ID NO:35:

(i) SEQUENCE CHARACTERISTICS:
(A) LENGTH: 7 amino acids
(B) TYPE: amino acid
(D) TOPOLOGY: linear (ii) MOLECULE TYPE: peptide (xi) SEQUENCE DESCRIPTION: SEQ ID NO:35:

Ser Phe Phe Leu Arg Asn Pro
1               5

(2) INFORMATION FOR SEQ ID NO:36:

(i) SEQUENCE CHARACTERISTICS:
(A) LENGTH: 5 amino acids
(B) TYPE: amino acid
(D) TOPOLOGY: linear (ii) MOLECULE TYPE: peptide (xi) SEQUENCE DESCRIPTION: SEQ ID NO:36:

```
        Phe  Leu  Leu  Arg  Asn
        1                   5
```

( 2 ) INFORMATION FOR SEQ ID NO:37:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:37:

```
        Ser  Phe  Ala  Leu  Arg
        1                   5
```

( 2 ) INFORMATION FOR SEQ ID NO:38:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Phe
            / note="Phe is n-propionyl Phe"

( x i ) SEQUENCE DESCRIPTION: SEQ ID NO:38:

```
        Phe  Leu  Leu  Arg
        1
```

( 2 ) INFORMATION FOR SEQ ID NO:39:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Phe
            / note="Phe is n-propionyl Phe"

( i x ) FEATURE:
        ( A ) NAME/KEY: Modified-site
        ( B ) LOCATION: 4
        ( D ) OTHER INFORMATION: /label=Arg
            / note="Arg is Arg-NH3"

( x i ) SEQUENCE DESCRIPTION: SEQ ID NO:39:

```
        Phe  Leu  Leu  Arg
        1
```

( 2 ) INFORMATION FOR SEQ ID NO:40:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:40:

```
        Ser  Phe  Leu  Leu  Lys
        1                   5
```

( 2 ) INFORMATION FOR SEQ ID NO:41:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:41:

Ala  Phe  Leu  Leu  Arg
    1                        5

( 2 ) INFORMATION FOR SEQ ID NO:42:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Ser
              / note="Ser is n-acetyl Ser"

( x i ) SEQUENCE DESCRIPTION: SEQ ID NO:42:

Ser  Phe  Leu  Leu  Arg
    1                        5

( 2 ) INFORMATION FOR SEQ ID NO:43:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 5
        ( D ) OTHER INFORMATION: /label=Arg
              / note="Arg is Arg-NH2"

( x i ) SEQUENCE DESCRIPTION: SEQ ID NO:43:

Ser  Phe  Leu  Leu  Arg
    1                        5

( 2 ) INFORMATION FOR SEQ ID NO:44:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 5
        ( D ) OTHER INFORMATION: /label=Arg
              / note="Arg is Arg-O-methyl"

( x i ) SEQUENCE DESCRIPTION: SEQ ID NO:44:

Ser  Phe  Leu  Leu  Arg
    1                        5

( 2 ) INFORMATION FOR SEQ ID NO:45:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 7
( D ) OTHER INFORMATION: /label=Pro
/ note="Pro is Pro-NH2"

( x i ) SEQUENCE DESCRIPTION: SEQ ID NO:45:

Ser Phe Leu Leu Arg Asn Pro
1               5

( 2 ) INFORMATION FOR SEQ ID NO:46:

( i ) SEQUENCE CHARACTERISTICS:
( A ) LENGTH: 5 amino acids
( B ) TYPE: amino acid
( D ) TOPOLOGY: linear ( i i ) MOLECULE TYPE: peptide ( x i ) SEQUENCE DESCRIPTION: SEQ ID NO:46:

Ser Phe Phe Leu Arg
1               5

( 2 ) INFORMATION FOR SEQ ID NO:47:

( i ) SEQUENCE CHARACTERISTICS:
( A ) LENGTH: 5 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 5
( D ) OTHER INFORMATION: /label=Arg
/ note="Arg is Arg-NH2"

( x i ) SEQUENCE DESCRIPTION: SEQ ID NO:47:

Ser Phe Phe Leu Arg
1               5

( 2 ) INFORMATION FOR SEQ ID NO:48:

( i ) SEQUENCE CHARACTERISTICS:
( A ) LENGTH: 5 amino acids
( B ) TYPE: amino acid
( D ) TOPOLOGY: circular ( i i ) MOLECULE TYPE: peptide ( x i ) SEQUENCE DESCRIPTION: SEQ ID NO:48:

Phe Leu Leu Arg Gly
1               5

( 2 ) INFORMATION FOR SEQ ID NO:49:

( i ) SEQUENCE CHARACTERISTICS:
( A ) LENGTH: 6 amino acids
( B ) TYPE: amino acid
( D ) TOPOLOGY: circular ( i i ) MOLECULE TYPE: peptide ( i x ) FEATURE:
    ( A ) NAME/KEY: Modified-site
    ( B ) LOCATION: 1
    ( D ) OTHER INFORMATION: /label=Xaa1
        / note="Xaa1 may be no AA, any nat/non-nat AA or derivative or a hydrophilic spacer"

( i x ) FEATURE:
    ( A ) NAME/KEY: Modified-site
    ( B ) LOCATION: 2
    ( D ) OTHER INFORMATION: /label=Xaa2
        / note="Xaa2 is a nat/non-nat basic AA or derivative"

( i x ) FEATURE:
    ( A ) NAME/KEY: Modified-site
    ( B ) LOCATION: 5
    ( D ) OTHER INFORMATION: /label=Xaa5
        / note="Xaa5 is a nat/non-nat aromatic AA or derivative"

( i x ) FEATURE:
    ( A ) NAME/KEY: Modified-site
    ( B ) LOCATION: 6
    ( D ) OTHER INFORMATION: /label=Ser
        / note="Ser is no AA or Ser"

( x i ) SEQUENCE DESCRIPTION: SEQ ID NO:49:

Xaa Xaa Leu Leu Xaa Ser
1                     5

( 2 ) INFORMATION FOR SEQ ID NO:50:

( i ) SEQUENCE CHARACTERISTICS:
        ( A ) LENGTH: 5 amino acids
        ( B ) TYPE: amino acid
        ( D ) TOPOLOGY: circular ( i i ) MOLECULE TYPE: peptide ( i x ) FEATURE:
        ( A ) NAME/KEY: Modified-site
        ( B ) LOCATION: 1
        ( D ) OTHER INFORMATION: /label=Xaa1
            / note="Xaa1 may be no AA, a nat/non-nat AA or derivative or a hydrophilic spacer"

( i x ) FEATURE:
        ( A ) NAME/KEY: Modified-site
        ( B ) LOCATION: 3
        ( D ) OTHER INFORMATION: /label=Xaa3
            / note="Xaa3 may be Pro, HyPro, Azc, Pip or Sar"

( i x ) FEATURE:
        ( A ) NAME/KEY: Modified-site
        ( B ) LOCATION: 5
        ( D ) OTHER INFORMATION: /label=Ser
            / note="Ser is no AA or Ser"

( x i ) SEQUENCE DESCRIPTION: SEQ ID NO:50:

Xaa Arg Xaa Phe Ser
1                 5